United States Patent
Cabiri et al.

(10) Patent No.: US 12,208,246 B2
(45) Date of Patent: Jan. 28, 2025

(54) BENT FLUID PATH ADD ON TO A PREFILLED FLUID RESERVOIR

(71) Applicant: West Pharma. Services IL, Ltd., Ra'anana (IL)

(72) Inventors: Oz Cabiri, Hod Hasharon (IL); Paul H. Norton, St. Augustine, FL (US); Ran Hezkiahu, Herzliya (IL); Richard Brough, Scottsdale, AZ (US)

(73) Assignee: West Pharma. Services IL, Ltd., Ra'anana (IL)

( * ) Notice: Subject to any disclaimer, the term of this patent is extended or adjusted under 35 U.S.C. 154(b) by 0 days.

(21) Appl. No.: 18/228,039

(22) Filed: Jul. 31, 2023

(65) Prior Publication Data
US 2023/0372624 A1 Nov. 23, 2023

Related U.S. Application Data

(60) Continuation of application No. 17/395,670, filed on Aug. 6, 2021, now Pat. No. 11,759,573, which is a
(Continued)

(51) Int. Cl.
*A61M 5/28* (2006.01)
*A61M 5/31* (2006.01)
(Continued)

(52) U.S. Cl.
CPC ............ *A61M 5/28* (2013.01); *A61M 5/3134* (2013.01); *A61M 5/3202* (2013.01);
(Continued)

(58) Field of Classification Search
CPC .... A61M 5/28; A61M 5/3134; A61M 5/3202; A61M 5/3204; A61M 5/34;
(Continued)

(56) References Cited

U.S. PATENT DOCUMENTS

| 232,432 A | 9/1880 | Allison |
|---|---|---|
| 1,125,887 A | 1/1915 | Schimmel |

(Continued)

FOREIGN PATENT DOCUMENTS

| CN | 1071846 | 5/1993 |
|---|---|---|
| CN | 1118273 | 3/1996 |

(Continued)

OTHER PUBLICATIONS

US 8,333,733 B2, 12/2012, Lanigan (withdrawn)
(Continued)

*Primary Examiner* — Tasnim Mehjabin Ahmed
(74) *Attorney, Agent, or Firm* — Blank Rome LLP

(57) ABSTRACT

An add-on for a self-injector is described. The add-on includes an adaptor having at a rigid and a bent fluid path. The adaptor is sized and fitted to sterilely couple the bent fluid path to a tip of a fluid reservoir. The add-on also includes a fastener sized and fitted to couple a body of the fluid reservoir to the self-injector. The internal diameter of the fastener is adjustable. The adaptor and the fastener couple to the self-injector to at least one of a plurality of reservoirs having different sizes and tip types. The self-injector can include a support plate with a plurality of attachment points. The fastener can be sized and fitted to couple to the body of the fluid reservoir and to at least one of the attachment points. A retention cantilever can releasably couple the at least one fastener to the support plate.

28 Claims, 7 Drawing Sheets

Related U.S. Application Data division of application No. 15/766,719, filed as application No. PCT/US2016/056213 on Oct. 10, 2016, now Pat. No. 11,116,908, which is a continuation of application No. 15/204,542, filed on Jul. 7, 2016, now Pat. No. 10,576,207.

(60) Provisional application No. 62/281,536, filed on Jan. 21, 2016, provisional application No. 62/284,806, filed on Oct. 9, 2015.

(51) Int. Cl.
| | |
|---|---|
| *A61M 5/32* | (2006.01) |
| *A61M 5/34* | (2006.01) |
| *B29C 33/12* | (2006.01) |
| *B65D 1/36* | (2006.01) |
| *B65D 5/50* | (2006.01) |
| *B65D 21/02* | (2006.01) |
| *B65D 25/10* | (2006.01) |
| *A61M 5/142* | (2006.01) |
| *A61M 5/145* | (2006.01) |
| *A61M 5/158* | (2006.01) |
| *B29L 31/00* | (2006.01) |

(52) U.S. Cl.
CPC ............ *A61M 5/3204* (2013.01); *A61M 5/34* (2013.01); *B29C 33/12* (2013.01); *B65D 1/36* (2013.01); *B65D 5/503* (2013.01); *B65D 21/0233* (2013.01); *B65D 25/108* (2013.01); *A61M 5/14248* (2013.01); *A61M 5/1456* (2013.01); *A61M 2005/1581* (2013.01); *A61M 2005/312* (2013.01); *A61M 2005/341* (2013.01); *A61M 2205/3306* (2013.01); *A61M 2207/00* (2013.01); *B29L 2031/7544* (2013.01)

(58) Field of Classification Search
CPC ............ A61M 5/14248; A61M 5/1456; A61M 2005/1581; A61M 2005/312; A61M 2005/341; A61M 2205/3306; A61M 2207/00
See application file for complete search history.

(56) References Cited

U.S. PATENT DOCUMENTS

| | | |
|---|---|---|
| 1,321,550 A | 11/1919 | Platt |
| 1,704,921 A | 3/1929 | Nicoll |
| 1,795,530 A | 3/1931 | Henry |
| 1,795,630 A | 3/1931 | Wilson |
| 2,453,590 A | 11/1948 | Poux |
| 2,589,426 A | 3/1952 | Ogle |
| 2,677,373 A | 5/1954 | Barradas |
| 2,702,547 A | 2/1955 | Glass |
| 2,860,635 A | 11/1958 | Wilburn |
| 3,203,269 A | 8/1965 | Perrine |
| 3,212,685 A | 10/1965 | Richard |
| 3,585,439 A | 6/1971 | Schneeberger |
| 3,623,474 A | 11/1971 | Heilman |
| 3,705,582 A | 12/1972 | Stumpf |
| 3,708,945 A | 1/1973 | Klettke |
| 3,794,028 A | 2/1974 | Mueller |
| 3,834,387 A | 9/1974 | Brown |
| 3,994,295 A | 11/1976 | Wulff |
| 4,085,747 A | 4/1978 | Lee |
| 4,189,065 A | 2/1980 | Herold |
| 4,195,636 A | 4/1980 | Behnke |
| 4,218,724 A | 8/1980 | Kaufman |
| 4,254,768 A | 3/1981 | Ty |
| 4,273,122 A | 6/1981 | Whitney |
| 4,300,554 A | 11/1981 | Hessberg |
| 4,324,262 A | 4/1982 | Hall |
| 4,403,987 A | 9/1983 | Gottinger |
| 4,425,120 A | 1/1984 | Sampson |
| 4,435,173 A | 3/1984 | Siposs |
| 4,465,478 A | 8/1984 | Sabelman |
| 4,502,488 A | 3/1985 | Degironimo |
| 4,504,263 A | 3/1985 | Steuer |
| 4,549,554 A | 10/1985 | Markham |
| 4,564,054 A | 1/1986 | Gustavsson |
| 4,565,543 A | 1/1986 | Bekkering |
| 4,583,974 A | 4/1986 | Kokernak |
| 4,585,439 A | 4/1986 | Michel |
| 4,599,082 A | 7/1986 | Grimard |
| 4,601,702 A | 7/1986 | Hudson |
| 4,636,201 A | 1/1987 | Ambrose |
| 4,664,654 A | 5/1987 | Strauss |
| 4,685,903 A | 8/1987 | Cable |
| 4,695,274 A | 9/1987 | Fox |
| 4,698,055 A | 10/1987 | Sealfon |
| 4,702,738 A | 10/1987 | Spencer |
| 4,704,105 A | 11/1987 | Adorjan |
| 4,710,178 A | 12/1987 | Henri |
| 4,729,208 A | 3/1988 | Galy |
| 4,735,311 A | 4/1988 | Lowe |
| 4,737,144 A | 4/1988 | Choksi |
| 4,772,272 A | 9/1988 | McFarland |
| 4,810,215 A | 3/1989 | Kaneko |
| 4,810,249 A | 3/1989 | Haber |
| 4,813,426 A | 3/1989 | Haber |
| 4,840,185 A | 6/1989 | Hernandez |
| 4,850,966 A | 7/1989 | Grau |
| 4,861,341 A | 8/1989 | Woodburn |
| 4,863,434 A | 9/1989 | Bayless |
| 4,867,743 A | 9/1989 | Vaillancourt |
| 4,874,383 A | 10/1989 | McNaughton |
| 4,882,575 A | 11/1989 | Kawahara |
| 4,886,499 A | 12/1989 | Cirelli |
| 4,892,521 A | 1/1990 | Laico |
| 4,897,083 A | 1/1990 | Martell |
| 4,900,310 A | 2/1990 | Ogle, II |
| 4,915,702 A | 4/1990 | Haber |
| 4,919,569 A | 4/1990 | Wittenzelliner |
| 4,919,596 A | 4/1990 | Slate |
| 4,923,446 A | 5/1990 | Page |
| 4,929,241 A | 5/1990 | Kulli |
| 4,950,241 A | 8/1990 | Ranford |
| 4,950,246 A | 8/1990 | Muller |
| 4,957,490 A | 9/1990 | Byrne |
| 4,964,866 A | 10/1990 | Szwarc |
| 4,994,045 A | 2/1991 | Ranford |
| 4,998,924 A | 3/1991 | Ranford |
| 5,019,051 A | 5/1991 | Hake |
| 5,051,109 A | 9/1991 | Simon |
| 5,062,828 A | 11/1991 | Waltz |
| D322,671 S | 12/1991 | Szwarc |
| 5,088,988 A | 2/1992 | Talonn |
| 5,109,850 A | 5/1992 | Blanco |
| 5,112,317 A | 5/1992 | Michel |
| 5,114,406 A | 5/1992 | Gabriel |
| 5,127,910 A | 7/1992 | Talonn |
| 5,131,816 A | 7/1992 | Brown |
| 5,147,326 A | 9/1992 | Talonn |
| 5,156,599 A | 10/1992 | Ranford |
| 5,190,521 A | 3/1993 | Hubbard |
| 5,217,437 A | 6/1993 | Talonn |
| 5,246,670 A | 9/1993 | Haber |
| 5,254,096 A | 10/1993 | Rondelet |
| 5,267,977 A | 12/1993 | Feeney, Jr. |
| 5,269,762 A | 12/1993 | Armbruster |
| 5,275,582 A | 1/1994 | Wimmer |
| 5,282,593 A | 2/1994 | Fast |
| 5,295,966 A | 3/1994 | Stern |
| 5,298,023 A | 3/1994 | Haber |
| 5,300,045 A | 4/1994 | Plassche, Jr. |
| 5,318,522 A | 6/1994 | D'Antonio |
| 5,338,311 A | 8/1994 | Mahurkar |
| 5,342,313 A | 8/1994 | Campbell |
| 5,348,544 A | 9/1994 | Sweeney |
| 5,366,498 A | 11/1994 | Brannan |
| 5,376,785 A | 12/1994 | Chin |

(56) References Cited

U.S. PATENT DOCUMENTS

| | | |
|---|---|---|
| 5,383,865 A | 1/1995 | Michel |
| D356,150 S | 3/1995 | Duggan |
| 5,415,645 A | 5/1995 | Friend |
| 5,456,360 A | 10/1995 | Griffin |
| 5,478,315 A | 12/1995 | Brothers |
| 5,478,316 A | 12/1995 | Bitdinger |
| 5,482,446 A | 1/1996 | Williamson |
| 5,496,274 A | 3/1996 | Graves |
| 5,501,665 A | 3/1996 | Jhuboo |
| 5,505,709 A | 4/1996 | Funderburk |
| D369,864 S | 5/1996 | Petersen |
| D370,011 S | 5/1996 | Lindeman |
| 5,562,624 A | 10/1996 | Righi |
| 5,562,686 A | 10/1996 | Sauer |
| 5,593,390 A | 1/1997 | Castellano |
| 5,609,580 A | 3/1997 | Kwiatkowski |
| 5,611,785 A | 3/1997 | Mito |
| 5,616,132 A | 4/1997 | Newman |
| 5,624,400 A | 4/1997 | Firth |
| 5,637,095 A | 6/1997 | Nason |
| 5,643,218 A | 7/1997 | Lynn |
| 5,645,530 A | 7/1997 | Boukhny |
| 5,645,955 A | 7/1997 | Maglica |
| 5,647,853 A | 7/1997 | Feldmann |
| 5,658,256 A | 8/1997 | Shields |
| 5,662,678 A | 9/1997 | Macklin |
| 5,672,160 A | 9/1997 | Oesterlind |
| 5,690,618 A | 11/1997 | Smith |
| 5,697,908 A | 12/1997 | Imbert |
| 5,697,916 A | 12/1997 | Schraga |
| D389,139 S | 1/1998 | Oross |
| 5,725,500 A | 3/1998 | Micheler |
| 5,728,075 A | 3/1998 | Levander |
| D393,314 S | 4/1998 | Meisner |
| 5,741,275 A | 4/1998 | Wyssmann |
| 5,766,186 A | 6/1998 | Faraz |
| 5,776,103 A | 7/1998 | Kriesel |
| 5,795,675 A | 8/1998 | Maglica |
| 5,800,420 A | 9/1998 | Gross |
| 5,807,375 A | 9/1998 | Gross |
| 5,810,167 A | 9/1998 | Fujii |
| 5,810,784 A | 9/1998 | Tamaro |
| 5,814,020 A | 9/1998 | Gross |
| 5,830,187 A | 11/1998 | Kriesel |
| 5,836,920 A | 11/1998 | Robertson |
| 5,848,991 A | 12/1998 | Gross |
| 5,851,197 A | 12/1998 | Marano |
| 5,858,001 A * | 1/1999 | Tsals ................ A61M 5/14248 604/232 |
| 5,858,008 A | 1/1999 | Capaccio |
| 5,868,710 A | 2/1999 | Battiato |
| 5,893,842 A | 4/1999 | Imbert |
| 5,894,015 A | 4/1999 | Rechtin |
| 5,919,167 A | 7/1999 | Mulhauser |
| 5,926,596 A | 7/1999 | Edwards |
| 5,931,814 A | 8/1999 | Alex |
| 5,941,850 A | 8/1999 | Shah |
| 5,944,699 A | 8/1999 | Barrelle |
| 5,948,392 A | 9/1999 | Haslwanter |
| 5,954,697 A | 9/1999 | Srisathapat |
| 5,957,895 A | 9/1999 | Sage |
| 5,968,011 A | 10/1999 | Larsen |
| 5,989,221 A | 11/1999 | Hjertman |
| 5,993,423 A | 11/1999 | Choi |
| 6,004,296 A | 12/1999 | Jansen |
| 6,004,297 A | 12/1999 | Steenfeldt-Jensen |
| D421,902 S | 3/2000 | Hill |
| 6,033,245 A | 3/2000 | Yamkovoy |
| 6,033,377 A | 3/2000 | Rasmussen |
| 6,045,533 A | 4/2000 | Kriesel |
| D424,626 S | 5/2000 | Goto |
| 6,064,797 A | 5/2000 | Crittendon |
| 6,074,369 A | 6/2000 | Sage |
| 6,079,979 A | 6/2000 | Riitano |
| 6,162,197 A | 12/2000 | Mohammad |
| 6,186,979 B1 | 2/2001 | Dysarz |
| 6,186,982 B1 | 2/2001 | Gross |
| 6,189,292 B1 | 2/2001 | Odell |
| 6,200,289 B1 | 3/2001 | Hochman |
| 6,200,296 B1 | 3/2001 | Dibiasi |
| D441,185 S | 5/2001 | Shimizu |
| 6,224,569 B1 | 5/2001 | Brimhall |
| D443,508 S | 6/2001 | Braaten |
| 6,248,093 B1 | 6/2001 | Moberg |
| D445,496 S | 7/2001 | Anderson |
| 6,270,481 B1 | 8/2001 | Mason |
| 6,277,095 B1 | 8/2001 | Kriesel |
| 6,277,098 B1 | 8/2001 | Klitmose |
| 6,277,099 B1 | 8/2001 | Strowe |
| 6,287,283 B1 | 9/2001 | Ljunggreen |
| 6,293,925 B1 | 9/2001 | Safabash |
| 6,302,633 B1 | 10/2001 | Poe |
| 6,336,729 B1 | 1/2002 | Pavelle |
| 6,345,968 B1 | 2/2002 | Shupe |
| 6,362,591 B1 | 3/2002 | Moberg |
| 6,377,848 B1 | 4/2002 | Garde |
| 6,391,005 B1 | 5/2002 | Lum |
| D460,551 S | 7/2002 | Swenson |
| 6,423,029 B1 | 7/2002 | Elsberry |
| D461,243 S | 8/2002 | Niedospial, Jr. |
| D461,244 S | 8/2002 | Niermann |
| D461,245 S | 8/2002 | Niermann |
| D465,026 S | 10/2002 | May |
| 6,458,102 B1 | 10/2002 | Mann |
| 6,485,461 B1 | 11/2002 | Mason |
| 6,485,465 B2 | 11/2002 | Moberg |
| 6,500,150 B1 | 12/2002 | Gross |
| 6,503,231 B1 | 1/2003 | Prausnitz |
| 6,511,336 B1 | 1/2003 | Turek |
| 6,517,517 B1 | 2/2003 | Farrugia |
| D471,274 S | 3/2003 | Diaz |
| D471,983 S | 3/2003 | Hippolyte |
| 6,530,900 B1 | 3/2003 | David |
| 6,554,800 B1 | 4/2003 | Nezhadian |
| 6,555,986 B2 | 4/2003 | Moberg |
| D474,543 S | 5/2003 | Lee |
| 6,558,351 B1 | 5/2003 | Steil |
| 6,565,541 B2 | 5/2003 | Sharp |
| 6,585,695 B1 | 7/2003 | Adair |
| 6,589,229 B1 | 7/2003 | Connelly |
| 6,595,956 B1 | 7/2003 | Gross |
| 6,595,960 B2 | 7/2003 | West |
| 6,613,015 B2 | 9/2003 | Sandstrom |
| 6,645,181 B1 | 11/2003 | Lavi |
| 6,652,482 B2 | 11/2003 | Hochman |
| D483,281 S | 12/2003 | Cobigo |
| 6,656,158 B2 | 12/2003 | Dwayne |
| 6,656,159 B2 | 12/2003 | Flaherty |
| 6,659,980 B2 | 12/2003 | Moberg |
| 6,673,033 B1 | 1/2004 | Sciulli |
| 6,679,862 B2 | 1/2004 | Diaz |
| 6,685,678 B2 | 2/2004 | Evans |
| 6,689,118 B2 | 2/2004 | Alchas |
| 6,699,218 B2 | 3/2004 | Flaherty |
| 6,719,141 B2 | 4/2004 | Heinz |
| 6,722,916 B2 | 4/2004 | Buccinna |
| D490,069 S | 5/2004 | Lee |
| 6,743,211 B1 | 6/2004 | Prausnitz |
| 6,749,587 B2 | 6/2004 | Flaherty |
| 6,752,783 B2 | 6/2004 | Hung |
| 6,752,787 B1 | 6/2004 | Causey, III |
| 6,767,336 B1 | 7/2004 | Kaplan |
| 6,768,425 B2 | 7/2004 | Flaherty |
| D495,303 S | 8/2004 | Coullahan |
| 6,786,890 B2 | 9/2004 | Preuthun |
| 6,800,071 B1 | 10/2004 | McConnell |
| 6,805,687 B2 | 10/2004 | Dextradeur |
| 6,817,990 B2 | 11/2004 | Yap |
| 6,824,529 B2 | 11/2004 | Gross |
| 6,843,782 B2 | 1/2005 | Gross |
| 6,854,620 B2 | 2/2005 | Ramey |
| 6,889,690 B2 | 5/2005 | Crowder |
| 6,905,298 B1 | 6/2005 | Haring |
| 6,907,679 B2 | 6/2005 | Yarborough |

(56) References Cited

U.S. PATENT DOCUMENTS

| | | |
|---|---|---|
| 6,908,452 B2 | 6/2005 | Diaz |
| 6,960,192 B1 | 11/2005 | Flaherty |
| 6,979,316 B1 | 12/2005 | Rubin |
| D514,097 S | 1/2006 | De Leon |
| 6,997,727 B1 | 2/2006 | Legrady |
| 7,001,360 B2 | 2/2006 | Veasey |
| 7,004,104 B1 | 2/2006 | Kundus |
| 7,004,929 B2 | 2/2006 | McWethy |
| 7,025,226 B2 | 4/2006 | Ramey |
| 7,033,338 B2 | 4/2006 | Vilks |
| 7,034,223 B2 | 4/2006 | Fan |
| 7,048,715 B2 | 5/2006 | Diaz |
| 7,060,054 B2 | 6/2006 | Nissels |
| 7,060,059 B2 | 6/2006 | Keith |
| 7,063,684 B2 | 6/2006 | Moberg |
| 7,066,909 B1 | 6/2006 | Peter |
| 7,094,221 B2 | 8/2006 | Veasey |
| 7,097,637 B2 | 8/2006 | Triplett |
| 7,112,187 B2 | 9/2006 | Karlsson |
| 7,128,727 B2 | 10/2006 | Flaherty |
| 7,129,389 B1 | 10/2006 | Watson |
| 7,144,384 B2 | 12/2006 | Gorman |
| 7,193,521 B2 | 3/2007 | Moberg |
| D544,092 S | 6/2007 | Lewis |
| 7,225,694 B2 | 6/2007 | Said |
| 7,247,149 B2 | 7/2007 | Beyerlein |
| 7,250,037 B2 | 7/2007 | Shermer |
| 7,267,669 B2 | 9/2007 | Staunton |
| D552,184 S | 10/2007 | Hussaini |
| RE39,923 E | 11/2007 | Blom |
| 7,291,132 B2 | 11/2007 | DeRuntz |
| 7,291,159 B2 | 11/2007 | Schmelzeisen-Redeker |
| 7,303,549 B2 | 12/2007 | Flaherty |
| 7,306,578 B2 | 12/2007 | Gray |
| 7,326,194 B2 | 2/2008 | Zinger |
| 7,344,385 B2 | 3/2008 | Chen |
| 7,364,570 B2 | 4/2008 | Gerondale |
| 7,377,912 B2 | 5/2008 | Graf |
| 7,390,312 B2 | 6/2008 | Barrelle |
| 7,390,314 B2 | 6/2008 | Stutz, Jr. |
| 7,407,493 B2 | 8/2008 | Mario |
| 7,418,880 B1 | 9/2008 | Smith |
| D578,210 S | 10/2008 | Muta |
| 7,442,186 B2 | 10/2008 | Blomquist |
| 7,455,663 B2 | 11/2008 | Bikovsky |
| 7,465,290 B2 | 12/2008 | Reilly |
| 7,468,055 B2 | 12/2008 | Prais |
| 7,488,181 B2 | 2/2009 | Van Haaster |
| 7,497,842 B2 | 3/2009 | Diaz |
| 7,500,963 B2 | 3/2009 | Westbye |
| 7,501,587 B2 | 3/2009 | English |
| 7,503,786 B2 | 3/2009 | Kato |
| 7,530,964 B2 | 5/2009 | Lavi |
| RE40,755 E | 6/2009 | McWethy |
| 7,540,858 B2 | 6/2009 | Dibiasi |
| 7,547,281 B2 | 6/2009 | Hayes |
| 7,565,208 B2 | 7/2009 | Harris |
| 7,569,050 B2 | 8/2009 | Moberg |
| D600,341 S | 9/2009 | Loerwald |
| 7,585,287 B2 | 9/2009 | Bresina |
| 7,588,559 B2 | 9/2009 | Aravena |
| 7,589,974 B2 | 9/2009 | Grady |
| D602,155 S | 10/2009 | Foley |
| D602,586 S | 10/2009 | Foley |
| 7,597,682 B2 | 10/2009 | Moberg |
| D604,835 S | 11/2009 | Conley |
| D604,839 S | 11/2009 | Crawford |
| 7,611,491 B2 | 11/2009 | Pickhard |
| 7,621,893 B2 | 11/2009 | Moberg |
| D605,287 S | 12/2009 | Crawford |
| 7,628,770 B2 | 12/2009 | Ethelfeld |
| 7,628,772 B2 | 12/2009 | McConnell |
| 7,628,782 B2 | 12/2009 | Adair |
| 7,637,891 B2 | 12/2009 | Wall |
| 7,637,899 B2 | 12/2009 | Woolston |
| 7,641,649 B2 | 1/2010 | Moberg |
| 7,658,734 B2 | 2/2010 | Adair |
| 7,660,627 B2 | 2/2010 | McNichols |
| 7,678,079 B2 | 3/2010 | Shermer |
| 7,682,338 B2 | 3/2010 | Griffin |
| 7,686,787 B2 | 3/2010 | Moberg |
| 7,699,829 B2 | 4/2010 | Harris |
| 7,699,833 B2 | 4/2010 | Moberg |
| 7,704,088 B2 | 4/2010 | Sakamoto |
| 7,704,227 B2 | 4/2010 | Moberg |
| 7,704,229 B2 | 4/2010 | Moberg |
| 7,704,231 B2 | 4/2010 | Pongpairochana |
| 7,708,717 B2 | 5/2010 | Estes |
| 7,713,238 B2 | 5/2010 | Mernoe |
| 7,713,240 B2 | 5/2010 | Istoc |
| 7,717,903 B2 | 5/2010 | Estes |
| 7,717,913 B2 | 5/2010 | Novak |
| 7,722,574 B2 | 5/2010 | Toman |
| 7,736,333 B2 | 6/2010 | Gillespie, III |
| 7,736,344 B2 | 6/2010 | Moberg |
| 7,744,589 B2 | 6/2010 | Mounce |
| D619,338 S | 7/2010 | Teichert |
| 7,749,194 B2 | 7/2010 | Edwards |
| 7,758,548 B2 | 7/2010 | Gillespie |
| 7,758,550 B2 | 7/2010 | Bollenbach |
| D622,685 S | 8/2010 | Garra |
| 7,766,867 B2 | 8/2010 | Lynch |
| 7,766,873 B2 | 8/2010 | Moberg |
| 7,776,030 B2 | 8/2010 | Estes |
| 7,780,636 B2 | 8/2010 | Radmer |
| 7,780,637 B2 | 8/2010 | Jerde |
| 7,789,857 B2 | 9/2010 | Moberg |
| 7,794,426 B2 | 9/2010 | Briones |
| 7,794,427 B2 | 9/2010 | Estes |
| 7,801,599 B2 | 9/2010 | Young |
| 7,806,868 B2 | 10/2010 | De Polo |
| 7,828,528 B2 | 11/2010 | Estes |
| 7,837,659 B2 | 11/2010 | Bush, Jr. |
| 7,846,132 B2 | 12/2010 | Gravesen |
| 7,850,658 B2 | 12/2010 | Faust |
| 7,854,723 B2 | 12/2010 | Hwang |
| 7,857,131 B2 | 12/2010 | Vedrine |
| 7,879,025 B2 | 2/2011 | Jacobson |
| 7,892,206 B2 | 2/2011 | Moberg |
| 7,901,382 B2 | 3/2011 | Daily |
| 7,905,867 B2 | 3/2011 | Veasey |
| 7,918,825 B2 | 4/2011 | O'Connor |
| 7,931,621 B2 | 4/2011 | Cross |
| 7,935,104 B2 | 5/2011 | Yodfat |
| 7,935,105 B2 | 5/2011 | Miller |
| 7,938,803 B2 | 5/2011 | Mernoe |
| 7,955,305 B2 | 6/2011 | Moberg |
| 7,967,784 B2 | 6/2011 | Pongpairochana |
| 7,967,795 B1 | 6/2011 | Cabiri |
| D640,920 S | 7/2011 | Giraud |
| 7,976,514 B2 | 7/2011 | Abry |
| 7,981,105 B2 | 7/2011 | Adair |
| 7,988,683 B2 | 8/2011 | Adair |
| 7,993,300 B2 | 8/2011 | Nyholm |
| 7,993,301 B2 | 8/2011 | Boyd |
| 7,998,111 B2 | 8/2011 | Moberg |
| 7,998,131 B2 | 8/2011 | Adair |
| 8,002,754 B2 | 8/2011 | Kawamura |
| 8,021,357 B2 | 9/2011 | Tanaka |
| 8,025,658 B2 | 9/2011 | Chong |
| D646,159 S | 10/2011 | Bellamah |
| 8,029,469 B2 | 10/2011 | Ethelfeld |
| 8,034,019 B2 | 10/2011 | Nair |
| 8,034,026 B2 | 10/2011 | Grant |
| 8,038,666 B2 | 10/2011 | Triplett |
| 8,057,431 B2 | 11/2011 | Woehr |
| 8,057,436 B2 | 11/2011 | Causey |
| 8,062,253 B2 | 11/2011 | Nielsen |
| 8,062,255 B2 | 11/2011 | Brunnberg |
| 8,062,257 B2 | 11/2011 | Moberg |
| 8,065,096 B2 | 11/2011 | Moberg |
| 8,066,694 B2 | 11/2011 | Wagener |
| D650,079 S | 12/2011 | Presta |
| D650,903 S | 12/2011 | Kosinski |

(56) References Cited

U.S. PATENT DOCUMENTS

| | | |
|---|---|---|
| D651,308 S | 12/2011 | Crawford |
| 8,086,306 B2 | 12/2011 | Katzman |
| D652,503 S | 1/2012 | Cameron, III |
| 8,105,279 B2 | 1/2012 | Mernoe |
| 8,105,293 B2 | 1/2012 | Pickhard |
| 8,114,046 B2 | 2/2012 | Covino |
| 8,114,064 B2 | 2/2012 | Alferness |
| 8,114,066 B2 | 2/2012 | Naef |
| 8,118,781 B2 | 2/2012 | Knopper |
| 8,121,603 B2 | 2/2012 | Zhi |
| 8,128,596 B2 | 3/2012 | Carter |
| D657,462 S | 4/2012 | Siroky |
| 8,147,446 B2 | 4/2012 | Yodfat |
| 8,151,169 B2 | 4/2012 | Bieth |
| 8,152,764 B2 | 4/2012 | Istoc |
| 8,152,770 B2 | 4/2012 | Reid |
| 8,152,779 B2 | 4/2012 | Cabiri |
| 8,152,793 B2 | 4/2012 | Antti |
| 8,157,693 B2 | 4/2012 | Waksmundzki |
| 8,157,769 B2 | 4/2012 | Cabiri |
| 8,162,674 B2 | 4/2012 | Cho |
| 8,162,923 B2 | 4/2012 | Adams |
| D660,420 S | 5/2012 | Shaw |
| 8,167,841 B2 | 5/2012 | Teisen-Simony |
| 8,172,591 B2 | 5/2012 | Wertz |
| 8,172,804 B2 | 5/2012 | Bikovsky |
| 8,177,749 B2 | 5/2012 | Slate |
| 8,182,447 B2 | 5/2012 | Moberg |
| 8,182,462 B2 | 5/2012 | Istoc |
| 8,197,444 B1 | 6/2012 | Bazargan |
| 8,206,351 B2 | 6/2012 | Sugimoto |
| 8,210,172 B2 | 7/2012 | Crowder |
| 8,221,356 B2 | 7/2012 | Enggaard |
| D667,382 S | 9/2012 | Cosentino |
| D667,950 S | 9/2012 | Hyun |
| 8,257,345 B2 | 9/2012 | Adair |
| 8,267,893 B2 | 9/2012 | Moberg |
| 8,267,921 B2 | 9/2012 | Yodfat |
| 8,273,061 B2 | 9/2012 | McConnell |
| 8,287,520 B2 | 10/2012 | Drew |
| 8,292,647 B1 | 10/2012 | McGrath |
| 8,303,549 B2 | 11/2012 | Mejlhede |
| 8,303,572 B2 | 11/2012 | Adair |
| 8,308,679 B2 | 11/2012 | Hanson |
| 8,308,695 B2 | 11/2012 | Laiosa |
| 8,313,467 B2 | 11/2012 | Chong |
| 8,323,250 B2 | 12/2012 | Chong |
| 8,348,898 B2 | 1/2013 | Cabiri |
| 8,366,668 B2 | 2/2013 | Maritan |
| 8,372,039 B2 | 2/2013 | Mernoe |
| 8,373,421 B2 | 2/2013 | Lindegger |
| 8,393,357 B2 | 3/2013 | Chong |
| 8,409,141 B2 | 4/2013 | Johansen |
| 8,409,142 B2 | 4/2013 | Causey |
| 8,409,143 B2 | 4/2013 | Lanigan |
| 8,409,149 B2 | 4/2013 | Hommann |
| 8,414,533 B2 | 4/2013 | Alexandersson |
| 8,414,557 B2 | 4/2013 | Istoc |
| 8,425,468 B2 | 4/2013 | Weston |
| 8,430,847 B2 | 4/2013 | Mernoe |
| D683,848 S | 6/2013 | Ogura |
| D684,686 S | 6/2013 | Cronenberg |
| D685,083 S | 6/2013 | Schneider |
| D685,084 S | 6/2013 | Guarraia |
| 8,465,455 B2 | 6/2013 | Cabiri |
| 8,469,942 B2 | 6/2013 | Kow |
| D687,140 S | 7/2013 | Guarraia |
| D687,141 S | 7/2013 | Schneider |
| 8,474,332 B2 | 7/2013 | Bente, IV |
| 8,475,408 B2 | 7/2013 | Mernoe |
| 8,479,595 B2 | 7/2013 | Vazquez |
| 8,483,980 B2 | 7/2013 | Moberg |
| 8,490,790 B2 | 7/2013 | Cocheteux |
| 8,495,918 B2 | 7/2013 | Bazargan |
| 8,496,862 B2 | 7/2013 | Zelkovich |
| D687,536 S | 8/2013 | Guarraia |
| D688,784 S | 8/2013 | Schneider |
| 8,500,716 B2 | 8/2013 | Adair |
| 8,512,287 B2 | 8/2013 | Cindrich |
| 8,512,295 B2 | 8/2013 | Evans |
| 8,517,987 B2 | 8/2013 | Istoc |
| 8,517,992 B2 | 8/2013 | Jones |
| 8,523,803 B1 | 9/2013 | Favreau |
| 8,545,469 B2 | 10/2013 | Andresen |
| 8,551,046 B2 | 10/2013 | Causey |
| 8,556,856 B2 | 10/2013 | Bazargan |
| 8,562,364 B2 | 10/2013 | Lin |
| 8,568,361 B2 | 10/2013 | Yodfat |
| 8,574,216 B2 | 11/2013 | Istoc |
| 8,603,026 B2 | 12/2013 | Favreau |
| 8,603,027 B2 | 12/2013 | Favreau |
| 8,603,028 B2 | 12/2013 | Mudd |
| 8,613,719 B2 | 12/2013 | Karratt |
| 8,617,110 B2 | 12/2013 | Moberg |
| 8,622,966 B2 | 1/2014 | Causey |
| 8,628,510 B2 | 1/2014 | Bazargan |
| 8,632,499 B2 | 1/2014 | Grant |
| 8,647,074 B2 | 2/2014 | Moberg |
| 8,647,296 B2 | 2/2014 | Moberg |
| 8,647,303 B2 | 2/2014 | Cowe |
| 8,668,672 B2 | 3/2014 | Moberg |
| 8,674,288 B2 | 3/2014 | Hanson |
| 8,679,060 B2 | 3/2014 | Mernoe |
| 8,681,010 B2 | 3/2014 | Moberg |
| D702,834 S | 4/2014 | Norton |
| 8,690,855 B2 | 4/2014 | Alderete, Jr. |
| 8,708,961 B2 | 4/2014 | Field |
| 8,715,237 B2 | 5/2014 | Moberg |
| 8,721,603 B2 | 5/2014 | Lundquist |
| 8,727,117 B2 | 5/2014 | Maasarani |
| 8,734,344 B2 | 5/2014 | Taub |
| 8,751,237 B2 | 6/2014 | Kubota |
| 8,753,326 B2 | 6/2014 | Chong |
| 8,753,331 B2 | 6/2014 | Murphy |
| 8,764,707 B2 | 7/2014 | Moberg |
| 8,764,723 B2 | 7/2014 | Chong |
| 8,771,222 B2 | 7/2014 | Kanderian, Jr. |
| 8,777,896 B2 | 7/2014 | Starkweather |
| 8,777,924 B2 | 7/2014 | Kanderian, Jr. |
| 8,777,925 B2 | 7/2014 | Patton |
| 8,784,369 B2 | 7/2014 | Starkweather |
| 8,784,370 B2 | 7/2014 | Lebel |
| 8,784,378 B2 | 7/2014 | Weinandy |
| 8,790,295 B1 | 7/2014 | Sigg |
| 8,795,224 B2 | 8/2014 | Starkweather |
| 8,795,231 B2 | 8/2014 | Chong |
| 8,795,260 B2 | 8/2014 | Drew |
| 8,801,668 B2 | 8/2014 | Ali |
| 8,801,679 B2 | 8/2014 | Iio |
| 8,810,394 B2 | 8/2014 | Kalpin |
| 8,814,379 B2 | 8/2014 | Griffiths |
| D714,266 S | 9/2014 | Okamura |
| 8,845,587 B2 | 9/2014 | Lanigan |
| D715,428 S | 10/2014 | Baid |
| 8,858,508 B2 | 10/2014 | Lavi |
| 8,864,739 B2 | 10/2014 | Moberg |
| 8,876,770 B2 | 11/2014 | Kraft |
| 8,876,778 B2 | 11/2014 | Carrel |
| 8,882,711 B2 | 11/2014 | Saulenas |
| 8,911,410 B2 | 12/2014 | Ekman |
| 8,915,882 B2 | 12/2014 | Cabiri |
| 8,915,886 B2 | 12/2014 | Cowe |
| 8,920,374 B2 | 12/2014 | Bokelman |
| 8,932,266 B2 | 1/2015 | Wozencroft |
| D722,870 S | 2/2015 | Fohner |
| 8,979,802 B2 | 3/2015 | Woehr |
| 8,986,250 B2 | 3/2015 | Beebe |
| 9,011,164 B2 | 4/2015 | Filman |
| 9,011,371 B2 | 4/2015 | Moberg |
| 9,011,387 B2 | 4/2015 | Ekman |
| 9,033,925 B2 | 5/2015 | Moberg |
| 9,061,104 B2 | 6/2015 | Daniel |
| 9,061,110 B2 | 6/2015 | Avery |
| 9,072,827 B2 | 7/2015 | Cabiri |

(56) References Cited

U.S. PATENT DOCUMENTS

| | | |
|---|---|---|
| 9,072,845 B2 | 7/2015 | Hiles |
| 9,084,668 B2 | 7/2015 | Hamas |
| 9,089,475 B2 | 7/2015 | Fangrow |
| 9,089,641 B2 | 7/2015 | Kavazov |
| 9,107,999 B2 | 8/2015 | Moberg |
| 9,138,534 B2 | 9/2015 | Yodfat |
| 9,149,575 B2 | 10/2015 | Cabiri |
| 9,173,996 B2 | 11/2015 | Gray |
| 9,173,997 B2 | 11/2015 | Gross |
| 9,180,248 B2 | 11/2015 | Moberg |
| D745,661 S | 12/2015 | Collins |
| 9,205,188 B2 | 12/2015 | Lanigan |
| 9,205,199 B2 | 12/2015 | Kemp |
| D747,799 S | 1/2016 | Norton |
| 9,233,215 B2 | 1/2016 | Hourmand |
| 9,259,532 B2 | 2/2016 | Cabiri |
| D751,699 S | 3/2016 | Mills |
| 9,283,327 B2 | 3/2016 | Hourmand |
| D753,810 S | 4/2016 | Chang |
| 9,308,318 B2 | 4/2016 | Lanigan |
| 9,308,319 B2 | 4/2016 | Mernoe |
| 9,308,327 B2 | 4/2016 | Marshall |
| 9,314,569 B2 | 4/2016 | Causey |
| 9,320,849 B2 | 4/2016 | Smith |
| D755,950 S | 5/2016 | Meliniotis |
| 9,327,073 B2 | 5/2016 | Moberg |
| 9,339,607 B2 | 5/2016 | Langley |
| 9,345,834 B2 | 5/2016 | Henley |
| 9,345,836 B2 | 5/2016 | Cabiri |
| 9,350,634 B2 | 5/2016 | Fadell |
| 9,352,090 B2 | 5/2016 | Brereton |
| D760,374 S | 6/2016 | Nagar |
| 9,364,606 B2 | 6/2016 | Cindrich |
| 9,364,608 B2 | 6/2016 | Moberg |
| 9,373,269 B2 | 6/2016 | Bergman |
| 9,381,300 B2 | 7/2016 | Smith |
| 9,393,365 B2 | 7/2016 | Cabiri |
| D764,047 S | 8/2016 | Bjelovuk |
| 9,421,323 B2 | 8/2016 | Cabiri |
| 9,421,337 B2 | 8/2016 | Kemp |
| 9,427,531 B2 | 8/2016 | Hourmand |
| 9,433,732 B2 | 9/2016 | Moberg |
| 9,433,733 B2 | 9/2016 | Moberg |
| 9,446,188 B2 | 9/2016 | Grant |
| 9,446,196 B2 | 9/2016 | Hourmand |
| 9,452,261 B2 | 9/2016 | Alon |
| D769,438 S | 10/2016 | Crosby |
| D770,037 S | 10/2016 | Schleicher |
| 9,463,280 B2 | 10/2016 | Cabiri |
| 9,463,889 B2 | 10/2016 | Schmitz |
| 9,468,720 B2 | 10/2016 | Mudd |
| 9,474,859 B2 | 10/2016 | Ekman |
| 9,492,614 B2 | 11/2016 | Kamen |
| 9,492,622 B2 | 11/2016 | Brereton |
| 9,498,573 B2 | 11/2016 | Smith |
| 9,522,234 B2 | 12/2016 | Cabiri |
| D776,262 S | 1/2017 | Tyce |
| D776,265 S | 1/2017 | Tyce |
| D777,331 S | 1/2017 | Jayalath |
| 9,539,384 B2 | 1/2017 | Servansky |
| 9,539,388 B2 | 1/2017 | Causey |
| 9,539,757 B2 | 1/2017 | Ramirez |
| 9,572,926 B2 | 2/2017 | Cabiri |
| 9,572,927 B2 | 2/2017 | Brüggemann |
| 9,579,452 B2 | 2/2017 | Adair |
| 9,579,471 B2 | 2/2017 | Carrel |
| 9,610,407 B2 | 4/2017 | Brüggemann |
| 9,656,019 B2 | 5/2017 | Cabiri |
| 9,656,021 B2 | 5/2017 | Brereton |
| 9,656,025 B2 | 5/2017 | Anders |
| D792,359 S | 7/2017 | Nakagawa |
| 9,707,356 B2 | 7/2017 | Hourmand |
| D794,806 S | 8/2017 | Kranz |
| 9,744,306 B2 | 8/2017 | Cowe |
| D801,538 S | 10/2017 | Rondoni |
| 9,775,948 B2 | 10/2017 | Bechmann |
| 9,782,545 B2 | 10/2017 | Gross |
| 9,789,247 B2 | 10/2017 | Kamen |
| 9,814,830 B2 | 11/2017 | Mernoe |
| 9,814,839 B2 | 11/2017 | Eaton |
| 9,827,369 B2 | 11/2017 | Cawthon |
| D806,232 S | 12/2017 | Hwang |
| 9,849,242 B2 | 12/2017 | Henley |
| 9,862,519 B2 | 1/2018 | Deutschle |
| D810,948 S | 2/2018 | Wielunski |
| D812,739 S | 3/2018 | Wolford |
| 9,999,722 B2 | 6/2018 | Yodfat |
| 10,010,681 B2 | 7/2018 | Koch |
| D825,356 S | 8/2018 | Yu |
| 10,076,356 B2 | 9/2018 | Hadvary |
| 10,086,145 B2 | 10/2018 | Cabiri |
| D836,568 S | 12/2018 | Miller |
| 10,143,794 B2 | 12/2018 | Lanigan |
| 10,149,943 B2 | 12/2018 | Bar-El |
| D838,367 S | 1/2019 | Norton |
| 10,166,335 B2 | 1/2019 | Reber |
| 10,207,048 B2 | 2/2019 | Gray |
| 10,207,051 B2 | 2/2019 | Cereda |
| 10,227,161 B2 | 3/2019 | Auerbach |
| 10,232,116 B2 | 3/2019 | Ekman |
| 10,258,740 B2 | 4/2019 | McLoughlin |
| D847,976 S | 5/2019 | Protasiewicz |
| 10,369,289 B2 | 8/2019 | Cabiri |
| 10,376,641 B2 | 8/2019 | Hirschel |
| 10,376,647 B2 | 8/2019 | Farris |
| 10,398,832 B2 | 9/2019 | Qin |
| 10,434,262 B2 | 10/2019 | Bendek |
| 10,500,352 B2 | 12/2019 | Grant |
| 10,549,079 B2 | 2/2020 | Burton |
| 10,561,798 B2 | 2/2020 | Holland |
| 10,576,213 B2 | 3/2020 | Gylleby |
| 10,576,220 B2 | 3/2020 | Armes |
| 10,583,260 B2 | 3/2020 | Kemp |
| 10,603,430 B2 | 3/2020 | Shor |
| 10,646,643 B2 | 5/2020 | Cabiri |
| 10,722,645 B2 | 7/2020 | Kamen |
| 10,729,847 B2 | 8/2020 | Gray |
| 10,758,679 B2 | 9/2020 | Bar-El |
| 10,842,942 B2 | 11/2020 | Iibuchi |
| 11,027,059 B2 | 6/2021 | Niklaus |
| 2001/0005781 A1 | 6/2001 | Bergens |
| 2001/0018937 A1 | 9/2001 | Nemoto |
| 2001/0025168 A1 | 9/2001 | Gross |
| 2001/0034502 A1 | 10/2001 | Moberg |
| 2001/0041869 A1 | 11/2001 | Causey |
| 2002/0010423 A1 | 1/2002 | Gross |
| 2002/0016569 A1 | 2/2002 | Critchlow |
| 2002/0029018 A1 | 3/2002 | Jeffrey |
| 2002/0040208 A1 | 4/2002 | Flaherty |
| 2002/0055711 A1 | 5/2002 | Lavi |
| 2002/0055718 A1 | 5/2002 | Hunt |
| 2002/0065488 A1 | 5/2002 | Suzuki |
| 2002/0107487 A1 | 8/2002 | Preuthun |
| 2002/0120186 A1 | 8/2002 | Keimel |
| 2002/0123740 A1 | 9/2002 | Flaherty |
| 2002/0151855 A1 | 10/2002 | Douglas |
| 2002/0161332 A1 | 10/2002 | Ramey |
| 2002/0169215 A1 | 11/2002 | Meng |
| 2002/0173748 A1 | 11/2002 | McConnell |
| 2002/0173769 A1 | 11/2002 | Gray |
| 2003/0009133 A1 | 1/2003 | Ramey |
| 2003/0014018 A1 | 1/2003 | Giambattista |
| 2003/0050602 A1 | 3/2003 | Pettis |
| 2003/0069518 A1 | 4/2003 | Daley |
| 2003/0088238 A1 | 5/2003 | Poulsen |
| 2003/0125671 A1 | 7/2003 | Aramata |
| 2003/0130618 A1 | 7/2003 | Gray |
| 2003/0135159 A1 | 7/2003 | Daily |
| 2003/0160683 A1 | 8/2003 | Blomquist |
| 2003/0167039 A1 | 9/2003 | Moberg |
| 2003/0171717 A1 | 9/2003 | Farrugia |
| 2003/0181868 A1 | 9/2003 | Swenson |
| 2003/0199825 A1 | 10/2003 | Flaherty |
| 2003/0216683 A1 | 11/2003 | Shekalim |

(56) References Cited

U.S. PATENT DOCUMENTS

| | | |
|---|---|---|
| 2003/0236498 A1 | 12/2003 | Gross |
| 2004/0000818 A1 | 1/2004 | Preuthun |
| 2004/0003493 A1 | 1/2004 | Adair |
| 2004/0010207 A1 | 1/2004 | Flaherty |
| 2004/0049160 A1 | 3/2004 | Hsieh |
| 2004/0049161 A1 | 3/2004 | Shearn |
| 2004/0082911 A1 | 4/2004 | Tiu |
| 2004/0092873 A1 | 5/2004 | Moberg |
| 2004/0116866 A1 | 6/2004 | Gorman |
| 2004/0122359 A1 | 6/2004 | Wenz |
| 2004/0122369 A1 | 6/2004 | Schriver |
| 2004/0127857 A1 | 7/2004 | Shemesh |
| 2004/0135078 A1 | 7/2004 | Mandro |
| 2004/0158172 A1 | 8/2004 | Hancock |
| 2004/0158205 A1 | 8/2004 | Savage |
| 2004/0186419 A1 | 9/2004 | Cho |
| 2004/0186441 A1 | 9/2004 | Graf |
| 2004/0210196 A1 | 10/2004 | Bush, Jr. |
| 2004/0254533 A1 | 12/2004 | Schriver |
| 2004/0260233 A1 | 12/2004 | Garibotto |
| 2005/0027255 A1 | 2/2005 | Lavi |
| 2005/0033234 A1 | 2/2005 | Sadowski |
| 2005/0038391 A1 | 2/2005 | Wittland |
| 2005/0064917 A1 | 3/2005 | Peng |
| 2005/0065466 A1 | 3/2005 | Vedrine |
| 2005/0065472 A1 | 3/2005 | Cindrich |
| 2005/0071487 A1 | 3/2005 | Lu |
| 2005/0113761 A1 | 5/2005 | Faust |
| 2005/0124940 A1 | 6/2005 | Martin |
| 2005/0154353 A1 | 7/2005 | Alheidt |
| 2005/0159706 A1 | 7/2005 | Wilkinson |
| 2005/0171476 A1 | 8/2005 | Judson |
| 2005/0171512 A1 | 8/2005 | Flaherty |
| 2005/0177136 A1 | 8/2005 | Miller |
| 2005/0197626 A1 | 9/2005 | Moberg |
| 2005/0197650 A1 | 9/2005 | Sugimoto |
| 2005/0203461 A1 | 9/2005 | Flaherty |
| 2005/0238507 A1 | 10/2005 | Diianni |
| 2005/0245956 A1 | 11/2005 | Steinemann |
| 2005/0283114 A1 | 12/2005 | Bresina |
| 2006/0013716 A1 | 1/2006 | Nason |
| 2006/0030816 A1 | 2/2006 | Zubry |
| 2006/0036216 A1 | 2/2006 | Rimlinger |
| 2006/0079767 A1 | 4/2006 | Gibbs |
| 2006/0095010 A1 | 5/2006 | Westbye |
| 2006/0095014 A1 | 5/2006 | Ethelfeld |
| 2006/0122577 A1 | 6/2006 | Poulsen |
| 2006/0124269 A1 | 6/2006 | Miyazaki |
| 2006/0173406 A1 | 8/2006 | Hayes |
| 2006/0173439 A1 | 8/2006 | Thorne, Jr. |
| 2006/0184154 A1 | 8/2006 | Moberg |
| 2006/0195029 A1 | 8/2006 | Shults |
| 2006/0206054 A1 | 9/2006 | Shekalim |
| 2006/0206057 A1 | 9/2006 | Deruntz |
| 2006/0211982 A1 | 9/2006 | Prestrelski |
| 2006/0229569 A1 | 10/2006 | Lavi |
| 2006/0264888 A1 | 11/2006 | Moberg |
| 2006/0264889 A1 | 11/2006 | Moberg |
| 2006/0264890 A1 | 11/2006 | Moberg |
| 2006/0264894 A1 | 11/2006 | Moberg |
| 2006/0270987 A1 | 11/2006 | Peter |
| 2006/0283465 A1 | 12/2006 | Nickel |
| 2006/0293722 A1 | 12/2006 | Slatkine |
| 2007/0021733 A1 | 1/2007 | Hansen |
| 2007/0025879 A1 | 2/2007 | Vandergaw |
| 2007/0049865 A1 | 3/2007 | Radmer |
| 2007/0073228 A1 | 3/2007 | Mernoe |
| 2007/0079894 A1 | 4/2007 | Kraus |
| 2007/0118405 A1 | 5/2007 | Campbell |
| 2007/0149921 A1 | 6/2007 | Michels |
| 2007/0167912 A1 | 7/2007 | Causey |
| 2007/0179444 A1 | 8/2007 | Causey |
| 2007/0185449 A1 | 8/2007 | Mernoe |
| 2007/0197954 A1 | 8/2007 | Keenan |
| 2007/0197968 A1 | 8/2007 | Pongpairochana |
| 2007/0203454 A1 | 8/2007 | Shermer |
| 2007/0233038 A1 | 10/2007 | Pruitt |
| 2007/0265568 A1 | 11/2007 | Tsals |
| 2007/0282269 A1 | 12/2007 | Carter |
| 2008/0021439 A1 | 1/2008 | Brittingham |
| 2008/0033367 A1 | 2/2008 | Haury |
| 2008/0033369 A1 | 2/2008 | Kohlbrenner |
| 2008/0033393 A1 | 2/2008 | Edwards |
| 2008/0051711 A1 | 2/2008 | Mounce |
| 2008/0051730 A1 | 2/2008 | Bikovsky |
| 2008/0059133 A1 | 3/2008 | Edwards |
| 2008/0097326 A1 | 4/2008 | Moberg |
| 2008/0097381 A1 | 4/2008 | Moberg |
| 2008/0097387 A1 | 4/2008 | Spector |
| 2008/0108951 A1 | 5/2008 | Jerde |
| 2008/0119794 A1 | 5/2008 | Alheidt |
| 2008/0119795 A1 | 5/2008 | Erskine |
| 2008/0140006 A1 | 6/2008 | Eskuri |
| 2008/0140014 A1 | 6/2008 | Miller |
| 2008/0140018 A1 | 6/2008 | Enggaard |
| 2008/0147004 A1 | 6/2008 | Mann |
| 2008/0167641 A1 | 7/2008 | Hansen |
| 2008/0188813 A1 | 8/2008 | Miller |
| 2008/0208138 A1 | 8/2008 | Lim |
| 2008/0215006 A1 | 9/2008 | Thorkild |
| 2008/0215013 A1 | 9/2008 | Felix-Faure |
| 2008/0215015 A1 | 9/2008 | Cindrich |
| 2008/0221523 A1 | 9/2008 | Moberg |
| 2008/0243087 A1 | 10/2008 | Enggaard |
| 2008/0249473 A1 | 10/2008 | Rutti |
| 2008/0262436 A1 | 10/2008 | Olson |
| 2008/0269687 A1 | 10/2008 | Chong |
| 2008/0269723 A1 | 10/2008 | Mastrototaro |
| 2008/0274630 A1 | 11/2008 | Shelton |
| 2008/0294143 A1 | 11/2008 | Tanaka |
| 2008/0306449 A1 | 12/2008 | Kristensen |
| 2008/0312601 A1 | 12/2008 | Cane |
| 2008/0319383 A1 | 12/2008 | Byland |
| 2008/0319416 A1 | 12/2008 | Yodfat |
| 2009/0012478 A1 | 1/2009 | Weston |
| 2009/0041805 A1 | 2/2009 | Walker |
| 2009/0048347 A1 | 2/2009 | Cohen |
| 2009/0054750 A1 | 2/2009 | Jennewine |
| 2009/0069784 A1 | 3/2009 | Estes |
| 2009/0076383 A1 | 3/2009 | Toews |
| 2009/0076453 A1 | 3/2009 | Mejlhede |
| 2009/0088694 A1 | 4/2009 | Carter |
| 2009/0088731 A1 | 4/2009 | Campbell |
| 2009/0093763 A1 | 4/2009 | Gonnelli |
| 2009/0093792 A1* | 4/2009 | Gross ............... A61M 5/31596 604/218 |
| 2009/0093793 A1 | 4/2009 | Gross |
| 2009/0105650 A1 | 4/2009 | Wiegel |
| 2009/0105663 A1 | 4/2009 | Brand |
| 2009/0124977 A1 | 5/2009 | Jensen |
| 2009/0143730 A1 | 6/2009 | De Polo |
| 2009/0143735 A1 | 6/2009 | De Polo |
| 2009/0149830 A1 | 6/2009 | Spector |
| 2009/0182277 A1 | 7/2009 | Carter |
| 2009/0182284 A1 | 7/2009 | Morgan |
| 2009/0204076 A1 | 8/2009 | Liversidge |
| 2009/0209896 A1 | 8/2009 | Selevan |
| 2009/0234319 A1 | 9/2009 | Marksteiner |
| 2009/0240240 A1 | 9/2009 | Hines |
| 2009/0253973 A1 | 10/2009 | Bashan |
| 2009/0259143 A1 | 10/2009 | Bakhtyari-Nejad-Esfahani |
| 2009/0259176 A1 | 10/2009 | Yairi |
| 2009/0281585 A1 | 11/2009 | Katzman |
| 2009/0299288 A1 | 12/2009 | Sie |
| 2009/0299290 A1 | 12/2009 | Moberg |
| 2009/0299397 A1 | 12/2009 | Ruan |
| 2009/0326459 A1 | 12/2009 | Shipway |
| 2009/0326509 A1 | 12/2009 | Muse |
| 2010/0010455 A1 | 1/2010 | Elahi |
| 2010/0018334 A1 | 1/2010 | Lessing |
| 2010/0030156 A1 | 2/2010 | Beebe |
| 2010/0030198 A1 | 2/2010 | Beebe |
| 2010/0049128 A1 | 2/2010 | McKenzie |
| 2010/0049144 A1 | 2/2010 | McConnell |

(56) References Cited

U.S. PATENT DOCUMENTS

| | | |
|---|---|---|
| 2010/0057057 A1 | 3/2010 | Hayter |
| 2010/0076382 A1 | 3/2010 | Weston |
| 2010/0076412 A1 | 3/2010 | Rush |
| 2010/0094255 A1 | 4/2010 | Nycz |
| 2010/0100076 A1 | 4/2010 | Rush |
| 2010/0100077 A1 | 4/2010 | Rush |
| 2010/0106098 A1 | 4/2010 | Atterbury |
| 2010/0121314 A1 | 5/2010 | Iobbi |
| 2010/0137790 A1 | 6/2010 | Yodfat |
| 2010/0137831 A1 | 6/2010 | Tsals |
| 2010/0145303 A1 | 6/2010 | Yodfat |
| 2010/0145305 A1 | 6/2010 | Alon |
| 2010/0160894 A1 | 6/2010 | Julian |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn |
| 2010/0204657 A1 | 8/2010 | Yodfat |
| 2010/0234767 A1 | 9/2010 | Sarstedt |
| 2010/0234830 A1 | 9/2010 | Straessler |
| 2010/0241065 A1 | 9/2010 | Moberg |
| 2010/0241103 A1 | 9/2010 | Kraft |
| 2010/0256486 A1 | 10/2010 | Savage |
| 2010/0264931 A1 | 10/2010 | Lindegger |
| 2010/0268169 A1 | 10/2010 | Llewellyn-Hyde |
| 2010/0274112 A1 | 10/2010 | Hoss |
| 2010/0274192 A1 | 10/2010 | Mernoe |
| 2010/0280499 A1 | 11/2010 | Yodfat |
| 2010/0331826 A1 | 12/2010 | Field |
| 2011/0022464 A1 | 1/2011 | Dunn |
| 2011/0028818 A1 | 2/2011 | Moberg |
| 2011/0034900 A1 | 2/2011 | Yodfat |
| 2011/0054399 A1 | 3/2011 | Chong |
| 2011/0054400 A1 | 3/2011 | Chong |
| 2011/0066131 A1 | 3/2011 | Cabiri |
| 2011/0092915 A1 | 4/2011 | Olson |
| 2011/0112504 A1 | 5/2011 | Causey |
| 2011/0125056 A1 | 5/2011 | Merchant |
| 2011/0160654 A1 | 6/2011 | Hanson |
| 2011/0160666 A1 | 6/2011 | Hanson |
| 2011/0160669 A1 | 6/2011 | Gyrn |
| 2011/0166509 A1 | 7/2011 | Gross |
| 2011/0166512 A1 | 7/2011 | Both |
| 2011/0172645 A1 | 7/2011 | Moga |
| 2011/0172745 A1 | 7/2011 | Na |
| 2011/0178463 A1 | 7/2011 | Cabiri |
| 2011/0178472 A1 | 7/2011 | Cabiri |
| 2011/0201998 A1 | 8/2011 | Pongpairochana |
| 2011/0224616 A1 | 9/2011 | Slate |
| 2011/0224646 A1 | 9/2011 | Yodfat |
| 2011/0238031 A1 | 9/2011 | Adair |
| 2011/0245773 A1 | 10/2011 | Estes |
| 2011/0270160 A1 | 11/2011 | Mernoe |
| 2011/0282282 A1 | 11/2011 | Lorenzen |
| 2011/0282296 A1 | 11/2011 | Harms |
| 2011/0288526 A1 | 11/2011 | Wei |
| 2011/0295205 A1 | 12/2011 | Kaufmann |
| 2011/0313238 A1 | 12/2011 | Reichenbach |
| 2011/0315269 A1 | 12/2011 | Williamson |
| 2011/0319861 A1 | 12/2011 | Wilk |
| 2011/0319919 A1 | 12/2011 | Curry |
| 2012/0004602 A1 | 1/2012 | Hanson |
| 2012/0010594 A1 | 1/2012 | Holt |
| 2012/0022344 A1 | 1/2012 | Kube |
| 2012/0022496 A1 | 1/2012 | Causey |
| 2012/0022499 A1 | 1/2012 | Anderson |
| 2012/0029431 A1 | 2/2012 | Hwang |
| 2012/0035546 A1 | 2/2012 | Cabiri |
| 2012/0041364 A1 | 2/2012 | Smith |
| 2012/0041387 A1 | 2/2012 | Bruggemann |
| 2012/0041414 A1 | 2/2012 | Estes |
| 2012/0071828 A1 | 3/2012 | Tojo |
| 2012/0096953 A1 | 4/2012 | Bente, IV |
| 2012/0096954 A1 | 4/2012 | Vazquez |
| 2012/0101436 A1 | 4/2012 | Bazargan |
| 2012/0108933 A1 | 5/2012 | Liang |
| 2012/0109059 A1 | 5/2012 | Ranalletta |
| 2012/0109066 A1 | 5/2012 | Chase |
| 2012/0118777 A1 | 5/2012 | Kakiuchi |
| 2012/0123387 A1 | 5/2012 | Gonzalez |
| 2012/0129362 A1 | 5/2012 | Hampo |
| 2012/0160033 A1 | 6/2012 | Kow |
| 2012/0165733 A1 | 6/2012 | Bazargan |
| 2012/0165780 A1 | 6/2012 | Bazargan |
| 2012/0172817 A1 | 7/2012 | Bruggemann |
| 2012/0184917 A1 | 7/2012 | Bom |
| 2012/0226234 A1 | 9/2012 | Bazargan |
| 2012/0238961 A1 | 9/2012 | Julian |
| 2012/0259282 A1 | 10/2012 | Alderete, Jr. |
| 2013/0012875 A1 | 1/2013 | Gross |
| 2013/0068319 A1 | 3/2013 | Plumptre |
| 2013/0085457 A1 | 4/2013 | Schiff |
| 2013/0089992 A1 | 4/2013 | Yang |
| 2013/0096509 A1 | 4/2013 | Avery |
| 2013/0110049 A1 | 5/2013 | Cronenberg |
| 2013/0131589 A1 | 5/2013 | Mudd |
| 2013/0131604 A1 | 5/2013 | Avery |
| 2013/0133438 A1 | 5/2013 | Kow |
| 2013/0138040 A1 | 5/2013 | Weinandy |
| 2013/0138078 A1 | 5/2013 | Smith |
| 2013/0153434 A1 | 6/2013 | Allanore |
| 2013/0172808 A1 | 7/2013 | Gilbert |
| 2013/0190693 A1 | 7/2013 | Ekman |
| 2013/0200549 A1 | 8/2013 | Felts |
| 2013/0204187 A1 | 8/2013 | Avery |
| 2013/0204191 A1 | 8/2013 | Cindrich |
| 2013/0237953 A1 | 9/2013 | Kow |
| 2013/0245595 A1 | 9/2013 | Kow |
| 2013/0245596 A1 | 9/2013 | Cabiri |
| 2013/0245604 A1 | 9/2013 | Kouyoumjian |
| 2013/0253419 A1 | 9/2013 | Favreau |
| 2013/0253420 A1 | 9/2013 | Favreau |
| 2013/0253421 A1 | 9/2013 | Favreau |
| 2013/0253434 A1 | 9/2013 | Cabiri |
| 2013/0253472 A1 | 9/2013 | Cabiri |
| 2013/0267895 A1 | 10/2013 | Hemmingsen |
| 2013/0296799 A1 | 11/2013 | Degtiar |
| 2013/0296824 A1 | 11/2013 | Mo |
| 2013/0304021 A1 | 11/2013 | Cabiri |
| 2013/0310753 A1 | 11/2013 | Cabiri |
| 2013/0310756 A1 | 11/2013 | Richard |
| 2013/0310807 A1 | 11/2013 | Adair |
| 2013/0323699 A1 | 12/2013 | Edwards |
| 2013/0331791 A1 | 12/2013 | Gross |
| 2013/0338584 A1 | 12/2013 | Mounce |
| 2014/0018735 A1 | 1/2014 | Causey |
| 2014/0031747 A1 | 1/2014 | Ardehali |
| 2014/0055073 A1 | 2/2014 | Favreau |
| 2014/0055076 A1 | 2/2014 | Favreau |
| 2014/0058349 A1 | 2/2014 | Bazargan |
| 2014/0083517 A1 | 3/2014 | Moia |
| 2014/0094755 A1 | 4/2014 | Bazargan |
| 2014/0121633 A1 | 5/2014 | Causey |
| 2014/0128807 A1 | 5/2014 | Moberg |
| 2014/0128815 A1 | 5/2014 | Cabiri |
| 2014/0128835 A1 | 5/2014 | Moberg |
| 2014/0135692 A1 | 5/2014 | Alderete, Jr. |
| 2014/0135694 A1 | 5/2014 | Moberg |
| 2014/0142499 A1 | 5/2014 | Moberg |
| 2014/0148784 A1 | 5/2014 | Anderson |
| 2014/0148785 A1 | 5/2014 | Moberg |
| 2014/0163522 A1 | 6/2014 | Alderete, Jr. |
| 2014/0163526 A1 | 6/2014 | Cabiri |
| 2014/0171881 A1 | 6/2014 | Cabiri |
| 2014/0174223 A1 | 6/2014 | Gross |
| 2014/0194819 A1 | 7/2014 | Maule |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0207067 A1 | 7/2014 | Kamen |
| 2014/0207104 A1 | 7/2014 | Vouillamoz |
| 2014/0213975 A1 | 7/2014 | Clemente |
| 2014/0214001 A1 | 7/2014 | Mortazavi |

(56) References Cited

U.S. PATENT DOCUMENTS

| | | |
|---|---|---|
| 2014/0228760 A1 | 8/2014 | Ethelfeld |
| 2014/0228768 A1 | 8/2014 | Eggert |
| 2014/0236087 A1 | 8/2014 | Alderete, Jr. |
| 2014/0243786 A1 | 8/2014 | Gilbert |
| 2014/0261758 A1 | 9/2014 | Wlodarczyk |
| 2014/0296784 A1 | 10/2014 | Lopez |
| 2014/0330240 A1 | 11/2014 | Cabiri |
| 2014/0343503 A1 | 11/2014 | Holmqvist |
| 2014/0346378 A1 | 11/2014 | Kua |
| 2014/0350459 A1 | 11/2014 | Lanier, Jr. |
| 2014/0364808 A1 | 12/2014 | Niklaus |
| 2015/0005703 A1 | 1/2015 | Hutchinson |
| 2015/0011965 A1 | 1/2015 | Cabiri |
| 2015/0073344 A1 | 3/2015 | Van Damme |
| 2015/0088071 A1 | 3/2015 | Cabiri |
| 2015/0112278 A1 | 4/2015 | Ray |
| 2015/0119798 A1 | 4/2015 | Gross |
| 2015/0157786 A1 | 6/2015 | Sonderegger |
| 2015/0157788 A1 | 6/2015 | Gescheit |
| 2015/0157806 A1 | 6/2015 | Knutsson |
| 2015/0165121 A1 | 6/2015 | Murakami |
| 2015/0165129 A1 | 6/2015 | Row |
| 2015/0180146 A1 | 6/2015 | Filman |
| 2015/0202375 A1 | 7/2015 | Schabbach |
| 2015/0250943 A1 | 9/2015 | Momose |
| 2015/0306307 A1 | 10/2015 | Cole |
| 2015/0359965 A1 | 12/2015 | O'Connor |
| 2015/0374926 A1 | 12/2015 | Gross |
| 2016/0030665 A1 | 2/2016 | Cabiri |
| 2016/0051756 A1 | 2/2016 | Cabiri |
| 2016/0058941 A1 | 3/2016 | Wu |
| 2016/0082184 A1 | 3/2016 | Hanagan |
| 2016/0089056 A1 | 3/2016 | Limaye |
| 2016/0121043 A1 | 5/2016 | Weibel |
| 2016/0135895 A1 | 5/2016 | Faasse |
| 2016/0144117 A1 | 5/2016 | Chun |
| 2016/0151586 A1 | 6/2016 | Kemp |
| 2016/0175515 A1 | 6/2016 | McCullough |
| 2016/0184512 A1 | 6/2016 | Marbet |
| 2016/0193406 A1 | 7/2016 | Cabiri |
| 2016/0199590 A1 | 7/2016 | Schabbach |
| 2016/0213840 A1 | 7/2016 | Schabbach |
| 2016/0220755 A1 | 8/2016 | Lanigan |
| 2016/0228652 A1 | 8/2016 | Cabiri |
| 2016/0256352 A1 | 9/2016 | Bar-El |
| 2016/0256353 A1 | 9/2016 | Bar-El |
| 2016/0284239 A1 | 9/2016 | Bergman |
| 2016/0296699 A1 | 10/2016 | Cabiri |
| 2016/0296711 A1 | 10/2016 | Blancke |
| 2016/0296713 A1 | 10/2016 | Schader |
| 2016/0296716 A1 | 10/2016 | Cabiri |
| 2016/0317738 A1 | 11/2016 | Cross |
| 2016/0331900 A1 | 11/2016 | Wei |
| 2016/0339168 A1 | 11/2016 | Hutchinson |
| 2016/0346478 A1 | 12/2016 | Bar-El |
| 2016/0354553 A1 | 12/2016 | Anderson |
| 2017/0007774 A1 | 1/2017 | Brockmeier |
| 2017/0021137 A1 | 1/2017 | Cole |
| 2017/0028132 A1 | 2/2017 | Cronenberg |
| 2017/0043092 A1 | 2/2017 | Murakami |
| 2017/0058349 A1 | 3/2017 | Levy |
| 2017/0080158 A1 | 3/2017 | Cabiri |
| 2017/0143907 A1 | 5/2017 | Stever |
| 2017/0175859 A1 | 6/2017 | Brockmeier |
| 2017/0224924 A1 | 8/2017 | Christensen |
| 2017/0246399 A1 | 8/2017 | Forlani |
| 2017/0246403 A1 | 8/2017 | Cowe |
| 2017/0340827 A1 | 11/2017 | Nazzaro |
| 2018/0028765 A1 | 2/2018 | Waller |
| 2018/0071454 A1 | 3/2018 | Betts |
| 2018/0133413 A1 | 5/2018 | Grant |
| 2018/0214637 A1 | 8/2018 | Kemp |
| 2018/0304029 A1 | 10/2018 | Koch |
| 2019/0022306 A1 | 1/2019 | Gibson |
| 2019/0060578 A1 | 2/2019 | Farris |
| 2019/0071217 A1 | 3/2019 | Brown |
| 2019/0099549 A1 | 4/2019 | Lanigan |
| 2019/0110749 A1 | 4/2019 | Forrester |
| 2019/0175821 A1 | 6/2019 | Kamen |
| 2019/0224415 A1 | 7/2019 | Dugand |
| 2019/0240417 A1 | 8/2019 | Hostettler |
| 2019/0298921 A1 | 10/2019 | Stafford |
| 2019/0328968 A1 | 10/2019 | Giambattista |
| 2019/0358441 A1 | 11/2019 | Zvezdin |
| 2019/0381239 A1 | 12/2019 | Cabiri |
| 2020/0009323 A1 | 1/2020 | Nair |
| 2020/0085349 A1 | 3/2020 | Bremer |
| 2020/0164151 A1 | 5/2020 | Farris |
| 2020/0215270 A1 | 7/2020 | Ogawa |
| 2020/0261643 A1 | 8/2020 | Boyaval |
| 2020/0297929 A1 | 9/2020 | Zhang |
| 2020/0316290 A1 | 10/2020 | Bourelle |
| 2020/0360602 A1 | 11/2020 | Gray |
| 2020/0405951 A1 | 12/2020 | Burren |
| 2021/0138157 A1 | 5/2021 | Bar-El |
| 2021/0220551 A1 | 7/2021 | Dowd |

FOREIGN PATENT DOCUMENTS

| | | |
|---|---|---|
| CN | 1211454 | 3/1999 |
| CN | 1440301 | 9/2003 |
| CN | 1476566 A | 2/2004 |
| CN | 1486198 | 3/2004 |
| CN | 1505535 A | 6/2004 |
| CN | 1646180 A | 7/2005 |
| CN | 1747683 A | 3/2006 |
| CN | 1753699 | 3/2006 |
| CN | 1863564 | 11/2006 |
| CN | 1863566 A | 11/2006 |
| CN | 1951513 | 4/2007 |
| CN | 101090749 A | 12/2007 |
| CN | 101128228 | 2/2008 |
| CN | 101227943 A | 7/2008 |
| CN | 101448536 A | 6/2009 |
| CN | 101460207 A | 6/2009 |
| CN | 101461976 | 6/2009 |
| CN | 101522235 A | 9/2009 |
| CN | 101522239 | 9/2009 |
| CN | 101541362 A | 9/2009 |
| CN | 101641126 A | 2/2010 |
| CN | 101687075 | 3/2010 |
| CN | 101784297 | 7/2010 |
| CN | 101868273 A | 10/2010 |
| CN | 201692438 U | 1/2011 |
| CN | 102038998 | 5/2011 |
| CN | 102149416 | 8/2011 |
| CN | 201941304 U | 8/2011 |
| CN | 102186733 A | 9/2011 |
| CN | 102378638 A | 3/2012 |
| CN | 102438679 | 5/2012 |
| CN | 102458512 | 5/2012 |
| CN | 102464145 | 5/2012 |
| CN | 202236675 | 5/2012 |
| CN | 102648016 | 8/2012 |
| CN | 102711868 | 10/2012 |
| CN | 102971032 | 3/2013 |
| CN | 103025369 | 4/2013 |
| CN | 103118737 | 5/2013 |
| CN | 103228303 | 7/2013 |
| CN | 103619378 | 3/2014 |
| CN | 103648561 | 3/2014 |
| CN | 103702699 | 4/2014 |
| CN | 103732277 | 4/2014 |
| CN | 103764197 | 4/2014 |
| CN | 103921966 | 7/2014 |
| CN | 103974734 | 8/2014 |
| CN | 103998082 | 8/2014 |
| CN | 203874209 | 10/2014 |
| CN | 104411350 | 3/2015 |
| CN | 104487116 | 4/2015 |
| CN | 104519933 | 4/2015 |
| CN | 104619366 | 5/2015 |
| CN | 105102025 A | 11/2015 |
| CN | 205107679 | 3/2016 |

(56) References Cited

FOREIGN PATENT DOCUMENTS

| | | |
|---|---|---|
| CN | 105749383 | 7/2016 |
| CN | 107007910 | 8/2017 |
| DE | 855313 C | 11/1952 |
| DE | 1064693 B | 9/1959 |
| DE | 19518807 A1 | 12/1995 |
| DE | 19717107 A1 | 11/1998 |
| EP | 0017412 A1 | 10/1980 |
| EP | 0222656 A1 | 5/1987 |
| EP | 0401179 A1 | 12/1990 |
| EP | 0851774 A1 | 7/1998 |
| EP | 0925082 A1 | 6/1999 |
| EP | 1003581 A1 | 5/2000 |
| EP | 1124600 A1 | 8/2001 |
| EP | 1219312 A2 | 7/2002 |
| EP | 1472477 A1 | 11/2004 |
| EP | 1530979 A1 | 5/2005 |
| EP | 1666080 A1 | 6/2006 |
| EP | 1372762 B1 | 2/2007 |
| EP | 1923081 A2 | 5/2008 |
| EP | 1974759 A1 | 10/2008 |
| EP | 2007455 B1 | 12/2008 |
| EP | 2060606 A1 | 5/2009 |
| EP | 2140897 A1 | 1/2010 |
| EP | 2173413 A1 | 4/2010 |
| EP | 2185227 A2 | 5/2010 |
| EP | 2192935 A1 | 6/2010 |
| EP | 1654018 | 11/2010 |
| EP | 2361648 A1 | 8/2011 |
| EP | 2364739 A1 | 9/2011 |
| EP | 2393534 A1 | 12/2011 |
| EP | 2452708 A1 | 5/2012 |
| EP | 2498589 A1 | 9/2012 |
| EP | 2574355 A1 | 4/2013 |
| EP | 2593162 | 5/2013 |
| EP | 2719410 A2 | 4/2014 |
| EP | 2393535 B1 | 3/2015 |
| EP | 2878320 A1 | 6/2015 |
| EP | 2878321 A1 | 6/2015 |
| EP | 2886144 A1 | 6/2015 |
| EP | 1904130 B1 | 3/2016 |
| EP | 2991705 A1 | 3/2016 |
| EP | 3266478 A1 | 1/2018 |
| EP | 2819724 B1 | 3/2019 |
| EP | 3498320 A1 | 6/2019 |
| FR | 2770136 A1 | 4/1999 |
| GB | 2301035 | 11/1996 |
| GB | 2436526 A | 10/2007 |
| JP | S62112566 A | 5/1987 |
| JP | H01172843 U | 12/1989 |
| JP | H05062828 A | 3/1993 |
| JP | H05237188 | 9/1993 |
| JP | H07194701 A | 8/1995 |
| JP | 3035448 U | 3/1997 |
| JP | H09505758 A | 6/1997 |
| JP | H1057489 | 3/1998 |
| JP | H1080486 | 3/1998 |
| JP | H11507260 A | 6/1999 |
| JP | 2000107289 A | 4/2000 |
| JP | 2000190163 | 7/2000 |
| JP | 2000515394 A | 11/2000 |
| JP | 2001512992 A | 8/2001 |
| JP | 2002505601 A | 2/2002 |
| JP | 2002507459 A | 3/2002 |
| JP | 2002528676 A | 9/2002 |
| JP | 2003501157 A | 1/2003 |
| JP | 2003527138 A | 9/2003 |
| JP | 2003534061 A | 11/2003 |
| JP | 2004501721 A | 1/2004 |
| JP | 3098104 | 2/2004 |
| JP | 2004512100 A | 4/2004 |
| JP | 2005523127 A | 8/2005 |
| JP | 2005527249 A | 9/2005 |
| JP | 2005270629 A | 10/2005 |
| JP | 2006507067 A | 3/2006 |
| JP | 2006510450 A | 3/2006 |
| JP | 2006525046 A | 11/2006 |
| JP | 2007509661 A | 4/2007 |
| JP | 2007517589 | 7/2007 |
| JP | 2007518455 | 7/2007 |
| JP | 2007249805 | 9/2007 |
| JP | 2007306990 A | 11/2007 |
| JP | 2008534131 A | 8/2008 |
| JP | 2008220961 A | 9/2008 |
| JP | 2008272084 | 11/2008 |
| JP | 2009502273 A | 1/2009 |
| JP | 2009101093 A | 5/2009 |
| JP | 2009205230 | 9/2009 |
| JP | 2009205342 | 9/2009 |
| JP | 2009539444 | 11/2009 |
| JP | 2010501281 A | 1/2010 |
| JP | 2010540054 A | 12/2010 |
| JP | 2010540156 A | 12/2010 |
| JP | 2011509133 | 3/2011 |
| JP | 2011136153 A | 7/2011 |
| JP | 2012023799 | 2/2012 |
| JP | 2012043553 | 3/2012 |
| JP | 2012059563 | 3/2012 |
| JP | 2012100927 A | 5/2012 |
| JP | 4947871 B2 | 6/2012 |
| JP | 2013500811 A | 1/2013 |
| JP | 2013505433 A | 2/2013 |
| JP | 2013516280 A | 5/2013 |
| JP | 2013517094 | 5/2013 |
| JP | 2013517095 A | 5/2013 |
| JP | 2013519473 A | 5/2013 |
| JP | D1441740 S | 5/2013 |
| JP | 2013530778 A | 8/2013 |
| JP | 2013531520 A | 8/2013 |
| JP | 2013531540 A | 8/2013 |
| JP | 2013192637 | 9/2013 |
| JP | 2014030489 A | 2/2014 |
| JP | 2014081861 | 5/2014 |
| JP | 2014515669 A | 7/2014 |
| JP | 2014518743 A | 8/2014 |
| JP | 2014521443 A | 8/2014 |
| JP | 2014525339 A | 9/2014 |
| JP | 2014211852 | 11/2014 |
| JP | 2015514486 A | 5/2015 |
| JP | 2015128613 | 7/2015 |
| JP | 2016517262 | 6/2016 |
| JP | 2016525428 A | 8/2016 |
| JP | 2016530016 A | 9/2016 |
| JP | 2017045775 | 3/2017 |
| JP | 2018047239 | 3/2018 |
| JP | 2019003830 | 1/2019 |
| JP | 2019500720 | 1/2019 |
| KR | 300689248 S | 4/2013 |
| MX | PA06003233 | 6/2006 |
| WO | 9009202 A1 | 8/1990 |
| WO | 9307922 A1 | 4/1993 |
| WO | 9407553 A1 | 4/1994 |
| WO | 9415660 A1 | 7/1994 |
| WO | 9513838 A1 | 5/1995 |
| WO | 9609083 A1 | 3/1996 |
| WO | 9632975 A1 | 10/1996 |
| WO | 9700091 A1 | 1/1997 |
| WO | 9710012 A1 | 3/1997 |
| WO | 9721457 A1 | 6/1997 |
| WO | 9733638 A1 | 9/1997 |
| WO | 9857683 A1 | 12/1998 |
| WO | 9857686 A1 | 12/1998 |
| WO | 9929151 A1 | 6/1999 |
| WO | 9938554 A1 | 8/1999 |
| WO | 9959665 A1 | 11/1999 |
| WO | 0025844 A1 | 5/2000 |
| WO | 0069509 A1 | 11/2000 |
| WO | 0130415 A2 | 5/2001 |
| WO | 0130421 A2 | 5/2001 |
| WO | 0152920 A2 | 7/2001 |
| WO | 0170304 A1 | 9/2001 |
| WO | 0172357 A2 | 10/2001 |
| WO | 0187384 A1 | 11/2001 |
| WO | 0189607 A2 | 11/2001 |
| WO | 0189613 A1 | 11/2001 |

(56) References Cited

FOREIGN PATENT DOCUMENTS

| | | |
|---|---|---|
| WO | 0202165 A2 | 1/2002 |
| WO | 0204049 A1 | 1/2002 |
| WO | 0234315 A1 | 5/2002 |
| WO | 0238204 A2 | 5/2002 |
| WO | 02056934 A2 | 7/2002 |
| WO | 02056943 A2 | 7/2002 |
| WO | 02072182 A1 | 9/2002 |
| WO | 03062672 A1 | 7/2003 |
| WO | 0390833 A1 | 11/2003 |
| WO | 2004000397 A1 | 12/2003 |
| WO | 2004032990 A2 | 4/2004 |
| WO | 2004073554 A2 | 9/2004 |
| WO | 2004098684 A2 | 11/2004 |
| WO | 2004105841 A1 | 12/2004 |
| WO | 2005018703 A2 | 3/2005 |
| WO | 2005037350 A2 | 4/2005 |
| WO | 2005070485 A1 | 8/2005 |
| WO | 2005072795 A2 | 8/2005 |
| WO | 2006018617 A1 | 2/2006 |
| WO | 2006037434 A1 | 4/2006 |
| WO | 2006052737 A1 | 5/2006 |
| WO | 2006069380 A1 | 6/2006 |
| WO | 2006102676 A1 | 9/2006 |
| WO | 2006104806 A2 | 10/2006 |
| WO | 2006121921 A2 | 11/2006 |
| WO | 2007017052 A1 | 2/2007 |
| WO | 2007051563 A1 | 5/2007 |
| WO | 2007056504 A1 | 5/2007 |
| WO | 2007066152 A2 | 6/2007 |
| WO | 2007073228 A1 | 6/2007 |
| WO | 2007106068 A2 | 9/2007 |
| WO | 2007119178 A2 | 10/2007 |
| WO | 2007141210 A1 | 12/2007 |
| WO | 2008001377 A2 | 1/2008 |
| WO | 2008014908 A1 | 2/2008 |
| WO | 2008057976 A2 | 5/2008 |
| WO | 2008072229 A2 | 6/2008 |
| WO | 2008076459 A1 | 6/2008 |
| WO | 2008078318 A2 | 7/2008 |
| WO | 2009019438 A1 | 2/2009 |
| WO | 2009022132 A2 | 2/2009 |
| WO | 2009039013 A1 | 3/2009 |
| WO | 2009043000 A1 | 4/2009 |
| WO | 2009043564 A1 | 4/2009 |
| WO | 2009044401 A2 | 4/2009 |
| WO | 2009046989 A2 | 4/2009 |
| WO | 2009069064 A1 | 6/2009 |
| WO | 2009125398 A2 | 10/2009 |
| WO | 2009144085 A2 | 12/2009 |
| WO | 2010078227 A1 | 7/2010 |
| WO | 2010078242 A1 | 7/2010 |
| WO | 2010089313 A1 | 8/2010 |
| WO | 2011054160 | 5/2011 |
| WO | 2011075105 A1 | 6/2011 |
| WO | 2011084951 A2 | 7/2011 |
| WO | 2011090955 A1 | 7/2011 |
| WO | 2011090956 A2 | 7/2011 |
| WO | 2011101378 A1 | 8/2011 |
| WO | 2011110872 A1 | 9/2011 |
| WO | 2011124631 A1 | 10/2011 |
| WO | 2011129175 A1 | 10/2011 |
| WO | 2011131778 A1 | 10/2011 |
| WO | 2011131780 A2 | 10/2011 |
| WO | 2011131781 A1 | 10/2011 |
| WO | 2011133823 A1 | 10/2011 |
| WO | 2011154160 A1 | 12/2011 |
| WO | 2011156373 A1 | 12/2011 |
| WO | 2012003221 A1 | 1/2012 |
| WO | 2012007246 | 1/2012 |
| WO | 2012032411 A2 | 3/2012 |
| WO | 2012040528 A1 | 3/2012 |
| WO | 2012145752 A2 | 10/2012 |
| WO | 2012160157 A1 | 11/2012 |
| WO | 2012168691 A1 | 12/2012 |
| WO | 2013036602 A1 | 3/2013 |
| WO | 2013058697 A1 | 4/2013 |
| WO | 2013115843 A1 | 8/2013 |
| WO | 2014049886 | 4/2014 |
| WO | 2014081411 A1 | 5/2014 |
| WO | 2014132293 A1 | 9/2014 |
| WO | 2014179117 A1 | 11/2014 |
| WO | 2014179774 A1 | 11/2014 |
| WO | 2014194183 A2 | 12/2014 |
| WO | 2015048791 A1 | 4/2015 |
| WO | 2015048803 A2 | 4/2015 |
| WO | 2015078868 A1 | 6/2015 |
| WO | 2015091758 A1 | 6/2015 |
| WO | 2015091850 A1 | 6/2015 |
| WO | 2015114158 A1 | 8/2015 |
| WO | 2015114428 A1 | 8/2015 |
| WO | 2015118358 A1 | 8/2015 |
| WO | 2015163009 A1 | 10/2015 |
| WO | 2016087626 A1 | 6/2016 |
| WO | 2016087627 A1 | 6/2016 |
| WO | 2016141082 A1 | 9/2016 |
| WO | 2016196934 | 12/2016 |
| WO | 2017022639 A1 | 2/2017 |
| WO | 2017161076 A1 | 9/2017 |
| WO | 2018222521 A1 | 12/2018 |
| WO | 2019224782 A1 | 11/2019 |
| WO | 2020023220 A1 | 1/2020 |
| WO | 2020120087 A1 | 6/2020 |
| WO | 2020193468 A1 | 10/2020 |

OTHER PUBLICATIONS

Office Action dated Aug. 29, 2014 in JP Application No. 2012-550068. 8 pages.
Office Action dated Aug. 29, 2014 in JP Application No. 2012-550069. 6 pages.
Office Action dated Sep. 28, 2017 in IN Application No. 2528/DELNP/2010.
Office Action dated Sep. 29, 2013 in CN Application No. 201080040968.7. 8 pages.
Office Action dated Sep. 30, 2010 in U.S. Appl. No. 12/689,250. 10 pages.
Office Action dated Sep. 30, 2015 in U.S. Appl. No. 13/667,739 by Cabiri. 11 pages.
Office Action dated Sep. 6, 2011 in U.S. Appl. No. 12/345,818. 6 pages.
Office Action dated Sep. 9, 2015 in U.S. Appl. No. 13/643,470 by Alon. 24 pages.
Office Action issued Aug. 17, 2021 in IN Application No. 201827027625.
Office Action dated Nov. 6, 2015 in U.S. Appl. No. 14/715,791 by Cabiri. 8 pages.
Search Report dated Nov. 24, 2015 in EP Application No. 14166592.7.
Search Report dated Oct. 14, 2016 in CN Application No. 2014101783742.
U.S. Appl. No. 60/997,459, filed Oct. 2, 2007.
Int'l Search Report and Written Opinion dated Jul. 31, 2014 in Int'l Application No. PCT/US2014/033598. 8 pages.
Int'l Search Report and Written Opinion dated May 13, 2009 in Int'l Application No. PCT/IL2008/001312. 16 pages.
Int'l Search Report dated Apr. 26, 2010 in Int'l Application No. PCT/US2009/069552. 8 pages.
Int'l Search Report dated Jun. 17, 2011 in Int'l Application No. PCT/US2011/021604. 8 pages.
Int'l Search Report dated Oct. 12, 2011 in Int'l Application No. PCT/US2011/021605.16 pages.
Int'l Search Report dated Sep. 22, 2011 in Int'l Application No. PCT/IL11/00368; Written Opinion. 8 pages.
Int'l Written Opinion dated Jul. 19, 2012 in Int'l Application No. PCT/US2011/021605.
International Preliminary Report on Patentability and Written Opinion issued Jul. 5, 2011 in International Application No. PCT/US2009/069552. 6 pages.

(56) References Cited

OTHER PUBLICATIONS

Notice of Allowance dated Aug. 24, 2015 in U.S. Appl. No. 29/479,307 by Norton. 10 pages.
Office Action dated Sep. 21, 2010 in U.S. Appl. No. 12/244,666. 12 pages.
Office Action dated Apr. 22, 2016 in CN Application No. 2014102892041.
Office Action dated Apr. 5, 2010 in U.S. Appl. No. 12/244,666. 11 pages.
Office Action dated Apr. 5, 2010 in U.S. Appl. No. 12/244,688. 14 pages.
Office Action dated Aug. 13, 2015 in U.S. Appl. No. 14/553,399 by Cabiri. 6 pages.
Office Action dated Aug. 14, 2017 in CN Application No. 201410178318.9.
Office Action dated Aug. 15, 2013 in CN Application No. 200880117084.X. 8 pages.
Office Action dated Aug. 26, 2014 in CN Application No. 201180006567.4. 10 pages.
Office Action dated Aug. 6, 2014 in EP Application No. 11 707 942.6. 4 pages.
Office Action dated Dec. 1, 2015 in CN Application No. 201410289204.1.
Office Action dated Dec. 10, 2013 in CN Application No. 201180006567.4. 8 pages.
Office Action dated Dec. 15, 2017 in U.S. Appl. No. 15/269,248, by Cabiri.
Office Action dated Dec. 12, 2013 in JP Application No. 2012-529808. 11 pages.
Office Action dated Dec. 4, 2017 in CN Application No. 201410178374.2.
Office Action dated Dec. 9, 2016 in U.S. Appl. No. 14/593,051, by Gross.
Office Action dated Feb. 16, 2017 in CN Application No. 2014101783189.
Office Action dated Feb. 20, 2015 in U.S. Appl. No. 13/521,181 by Cabiri. 13 pages.
Office Action dated Feb. 21, 2012 in U.S. Appl. No. 12/689,249. 6 pages.
Office Action dated Feb. 24, 2015 in U.S. Appl. No. 14/258,661 by Cabiri. 7 pages.
Office Action dated Feb. 24, 2017 in U.S. Appl. No. 13/964,651, by Gross.
Office Action dated Feb. 28, 2014 in CN Application No. 201180006571.0.
Office Action dated Feb. 4, 2014 in EP Application No. 11 707 942.6. 6 pages.
Office Action dated Jan. 10, 2017 in U.S. Appl. No. 14/193,692, by Gross.
Office Action dated Jan. 8, 2014 in U.S. Appl. No. 13/521,167 by Cabiri. 7 pages.
Office Action dated Jul. 13, 2011 in U.S. Appl. No. 12/559,563. 9 pages.
Office Action dated Jul. 2, 2012 in U.S. Appl. No. 13/272,555. 13 pages. 13 pages.
Office Action dated Jul. 3, 2017 in CN Application No. 201410178374.2.
Office Action dated Jul. 31, 2015 in U.S. Appl. No. 13/521,181 by Cabiri. 11 pages.
Int'l Preliminary Report on Patentability dated Jan. 18, 2018 in Int'l Application No. PCT/US2016/056213.
Int'l Preliminary Report on Patentability dated Jul. 16, 2015 in Int'l Application No. PCT/US2013/078040. 9 pages.
Int'l Preliminary Report on Patentability dated May 14, 2015 in Int'l Application No. PCT/US2013/065211. 10 pages.
Int'l Preliminary Report on Patentability dated Nov. 27, 2014 in Int'l Application No. PCT/US2013/039465. 8 pages.
Int'l Preliminary Report on Patentability dated Nov. 30, 2017 in Int'l Application No. PCT/US2016/068367.
Int'l Preliminary Report on Patentability dated Nov. 9, 2018 in Int'l Application No. PCT/US2016/056238.
Int'l Preliminary Report on Patentability dated Oct. 9, 2014 in Int'l Application No. PCT/US2013/033118. 7 pages.
Int'l Preliminary Report on Patentability dated Sep. 1, 2011 in Int'l Application No. PCT/US2010/048556. 6 pages.
Int'l Search Report and Written Opinion dated Apr. 3, 2014 in Int'l Application No. PCT/US2013/078040. 10 pages.
Int'l Search Report and Written Opinion dated Aug. 5, 2013 in Int'l Application No. PCT/US2013/033118. 9 pages.
Int'l Search Report and Written Opinion dated Jan. 7, 2014 in Int'l Application No. PCT/US2013/065211. 13 pages.
Int'l Search Report and Written Opinion dated Jul. 12, 2017 in Int'l Application No. PCT/US2016/056238.
Int'l Search Report and Written Opinion dated Nov. 5, 2012 in Int'l Application No. PCT/US2012/039465. 11 pages.
Office Action dated Mar. 1, 2018 in EP Application No. 14166592.7.
Office Action dated Mar. 10, 2015 in CN Application No. 201180006567.4. 9 pages.
Office Action dated Mar. 10, 2015 in U.S. Appl. No. 12/244,666 by Gross. 17 pages.
Office Action dated Mar. 10, 2015 in U.S. Appl. No. 13/643,470 by Alon. 16 pages.
Office Action dated Mar. 30, 2018 in U.S. Appl. No. 14/850,450 by Gross.
Office Action dated Mar. 23, 2015 in JP Application No. 2012-550068. 6 pages.
Office Action dated May 1, 2015 in U.S. Appl. No. 14/638,525 by Filman. 6 pages.
Office Action dated May 13, 2015 in CN Application No. 201380025566.3. 6 pages.
Office Action dated May 14, 2018 in EP Application No. 08808111.2.
Office Action dated May 16, 2012 in U.S. Appl. No. 12/615,828. 10 pages.
Office Action dated May 18, 2018 in EP 14166591.9.
Office Action dated May 23, 2014 in U.S. Appl. No. 13/472,112 by Cabiri. 9 pages.
Office Action dated May 24, 2017 in U.S. Appl. No. 13/874,121, by Degtiar.
Office Action dated May 21, 2021 in JP Application No. 2018-538073.
Office Action dated May 3, 2012 in CN Application No. 200880117084.X. 8 pages.
Office Action dated May 31, 2016 in U.S. Appl. No. 14/593,051 by Gross.
Office Action dated May 4, 2017 in CN Application No. 201410183666.5.
Office Action dated May 5, 2015 in CN Application No. 201180006571.0.
Office Action dated Apr. 23, 2015 in JP Application No. 2012-550069. 6 pages.
Office Action dated Nov. 10, 2016 in U.S. Appl. No. 13/874,121, by Degtiar.
Office Action dated Nov. 13, 2017 in U.S. Appl. No. 14/193,692, by Gross.
Office Action dated Nov. 2, 2014 in CN Application No. 201180006571.0. 8 pages.
Office Action dated Nov. 21, 2014 in U.S. Appl. No. 13/429,840 by Cabiri. 10 pages.
Office Action dated Nov. 21, 2014 in U.S. Appl. No. 13/472,112 by Cabiri. 10 pages.
Office Action dated Nov. 25, 2016 in U.S. Appl. No. 13/874,017, by Cabiri.
Office Action dated Nov. 4, 2013 in EP Application No. 11 709 234.6. 4 pages.
Office Action dated Nov. 5, 2013 in JP Application No. 2010-527595. 6 pages.
Office Action dated Nov. 5, 2014 in U.S. Appl. No. 13/643,470 by Alon. 15 pages.
Office Action dated Nov. 8, 2017 in U.S. Appl. No. 13/874,121, by Degtiar.

(56) References Cited

OTHER PUBLICATIONS

Office Action dated Oct. 9, 2020 in JP Application No. 2018-538073.
Office Action dated Oct. 28, 2011 in U.S. Appl. No. 12/615,828. 10 pages.
Office Action dated Oct. 28, 2016 in CN Application No. 201410178374.2.
Office Action issued Oct. 5, 2016 in U.S. Appl. No. 13/964,651, by Gross.
Office Action dated Oct. 6, 2017 in U.S. Appl. No. 14/861,478, by Cabiri.
Office Action dated Oct. 9, 2014 in U.S. Appl. No. 13/873,335. 6 pages.
Office Action dated Sep. 18, 2015 in U.S. Appl. No. 13/874,085 by Cabiri. 11 pages.
Office Action dated Sep. 2, 2010 in U.S. Appl. No. 12/244,688. 9 pages.
Office Action dated Jul. 7, 2014 in U.S. Appl. No. 12/244,666 by Gross. 16 pages.
Office Action dated Jun. 10, 2016 in U.S. Appl. No. 13/964,651 by Gross.
Office Action dated Jun. 14, 2018 in U.S. Appl. No. 13/874,121, by Degtiar.
Office Action dated Jun. 2, 2016 in CN Application No. 2014101783189.
Office Action dated Jun. 3, 2014 in JP Application No. 2010-527595. 8 pages.
Office Action dated Jun. 4, 2015 in U.S. Appl. No. 13/667,739 by Cabiri. 10 pages.
Office Action dated Jun. 9, 2017 in EP Application No. 14166591.9.
Office Action dated Jun. 9, 2017 in EP Application No. 14166596.8.
Int'l Preliminary Report on Patentability dated Jul. 10, 2019 in Int'l Application No. PCT/US2017/038527.
Office Action issued Mar. 23, 2021 in JP Application No. 2019-543787.
Office Action issued Apr. 14, 2021 in EP Application No. 17734924.8.
Office Action issued Feb. 28, 2014 in CN Application No. 201180006571.0. 9 pages.
Office Action issued Jan. 8, 2013 in JP Application No. 2010-527595. 8 pages.
Int'l Preliminary Report on Patentability dated Jun. 25, 2020 in Int'l Application No. PCT/US2019/023646.
Int'l Search Report and Written Opinion dated Jul. 22, 2019 in PCT Application No. PCT/US2019/023646.
Int'l Search Report and Written Opinion issued Feb. 17, 2020 in Int'l Application No. PCT/US2019/060740.
Int'l Preliminary Report on Patentability issued Feb. 12, 2021 in Int'l Application No. PCT/US2019/060740.
Office Action (Final Rejection) dated Mar. 16, 2023 for U.S. Appl. No. 17/395,670 (pp. 1-8).
Int'l Search Report and Written Opinion dated Dec. 15, 2016 in Int'l Application No. PCT/US2016/056258.
Int'l Search Report and Written Opinion dated Dec. 8, 2016 in Int'l Application No. PCT/US2016/056227.
Int'l Search Report and Written Opinion dated Nov. 30, 2016 in Int'l Application No. PCT/US2016/056223.
Int'l Search Report and Written Opinion dated Dec. 2, 2016 in Int'l Application No. PCT/US2016/056210.
Int'l Search Report and Written Opinion dated Nov. 28, 2016 in Int'l Application No. PCT/US2016/056218.
Int'l Search Report (Partial), dated Dec. 20, 2016 in Int'l Application No. PCT/US2016/056247.
Int'l Search Report and Written Opinion dated Dec. 5, 2016 in Int'l Application No. PCT/US2016/056233.
Int'l Search Report and Written Opinion dated Apr. 21, 2017 in Int'l Application No. PCT/US2016/068367.
Int'l Search Report and Written Opinion dated May 15, 2017 in Int'l Application No. PCT/US2016/068371.
Int'l Search Report and Written Opinion dated Mar. 27, 2017 in Int'l Application No. PCT/US2016/056247.
Int'l Search Report and Written Opinion dated Jan. 26, 2017 in Int'l Application No. PCT/US2016/056213.
European Search Report (Partial) dated Mar. 8, 2017 in EP Application 16193157.1. 7 pages.
Extended Search Report dated Jul. 7, 2017 in EP Application No. 16193157.1. 14 pages.
Office Action dated Mar. 2, 2018 in U.S. Appl. No. 29/597,876 by Norton.
Reynolds, "Integrated Solutions for the Delivery of High-Volume Biologics", West Pharmaceutical Services, www.ondrugdelivery.com, Copyright 2014, 4 pages.
Amgen Inc., "The Neulasta Onpro Kit", http://www.neulastahcp.com/neulasta-onpro/, Copyright 2016, 16 pages.
BD Worldwide, "Self-Injection Systems", http://www.bd.com/pharmaceuticals/products/self-injection/patch-injectors.asp, Copyright 2017, 2 pages.
Ondrugdelivery, "Wearable Injectors", Sep. 19, 2016 Issue No. 70, 48 pages.
Sensile Medical AG, "SensePatch", https://www.sensile-medical.com/assets/data-sheet_5002_senspatch.pdf, 2017, 2 pages.
Unilife Corporation, "Wearable Injectors", http://www.unilife.com/product-platforms/WearableInjectors, Copyright 2016, 3 pages.
West Pharmaceutical Services, Inc. "SmartDose Platform" http://www.westpharma.com/products/self-injection-platforms/smartdoes, Copyright 2017, 3 pages.
Int'l Preliminary Report on Patentability dated Jan. 18, 2018 in Int'l Application No. PCT/US2016/056227.
Office Action dated Sep. 26, 2018 in JP Application No. 2018-535062.
Int'l Preliminary Report on Patentability dated Jan. 18, 2018 in Int'l Application No. PCT/US2016/056223.
Communication Pursuant to Rules 161 and 162 dated Apr. 6, 2018 in EP Application No. 16784688.0. 3 pages.
Int'l Preliminary Report on Patentability dated Jan. 18, 2018 in Int'l Application No. PCT/US2016/056210.
Int'l Preliminary Report on Patentability date Jan. 8, 2018 in Int'l Application No. PCT/US2016/056218.
Office Action dated Jul. 22, 2020 in Japanese Application No. 2018-538074.
Extended European Search Report dated Jul. 28, 2020 in European Application No. 20172466.3. 8 pages.
Office Action dated Sep. 29, 2020 in JP Application No. 2018-538527.
Copaxone®, Innovative Drugs, Teva Pharmaceuticals, downloaded from webpage: http://tevapharm.com/copaxone/, Download date: Jan. 2009, original posting date: unknown, 3 pages.
Daikyo Crystal Zenith® polymer, Manufactured by Daikyo Seiko, Ltd. (Jun. 25, 2008). 2 pages.
Definition of Monolithic. In Merriam-Webster's online dictionary. Retrieved from https://www.merriam-webster.com/dictionary/monolithic (Year 2021).
Office Action dated Jan. 30, 2013 in CN Application No. 200880117084.X. 8 pages.
Office Action dated Mar. 5, 2014 in CN Application No. 200880117084.X. 8 pages.
Extended European Search Report dated Aug. 7, 2014 in EP Application No. 14174777.4. 7 pages.
Extended European Search Report dated Feb. 12, 2018 in EP Application No. 17191756.0. 8 pages.
Extended European Search Report dated Feb. 13, 2017 in EP Application No. 16171626.1. 9 pages.
Extended European Search Report dated Feb. 23, 2015 in EP Application No. 14166591.9. 6 pages.
Extended European Search Report dated Feb. 23, 2015 in EP Application No. 14166596.8. 6 pages.
Extended European Search Report dated Jul. 3, 2017 in EP Application No. 16190054.3. 7 pages.
Extended European Search Report dated Mar. 27, 2014 in EP Application No. 14154717.4. 6 pages.
Extended European Search Report dated Mar. 8, 2016 in EP Application No. 14166592.7. 11 pages.
Extended European Search Report dated Nov. 10, 2016 in EP Application No. 08808111.2. 9 pages.

(56) References Cited

OTHER PUBLICATIONS

Int'l Preliminary Report on Patentability dated Nov. 22, 2017 in Int'l Application No. PCT/US2016/068371.
Int'l Search Report and Written Opinion dated Jan. 12, 2011 in Int'l Application No. PCT/US2010/048556; Written Opinion. 9 pages.
Int'l Search Report and Written Opinion dated Jul. 6, 2017 in Int'l Application No. PCT/US2017/022966.
Int'l Preliminary Report on Patentability dated Apr. 7, 2010 in Int'l Application No. PCT/IL2008/001312. 14 pages.
Int'l Preliminary Report on Patentability dated Aug. 2, 2012 in Int'l Application No. PCT/US2011/021604. 6 pages.
Int'l Preliminary Report on Patentability dated Feb. 7, 2013 in Int'l Application No. PCT/US2011/021605. 9 pages.

* cited by examiner

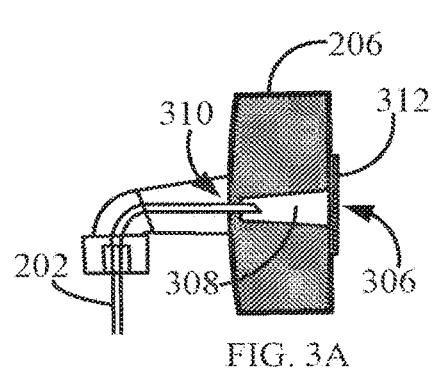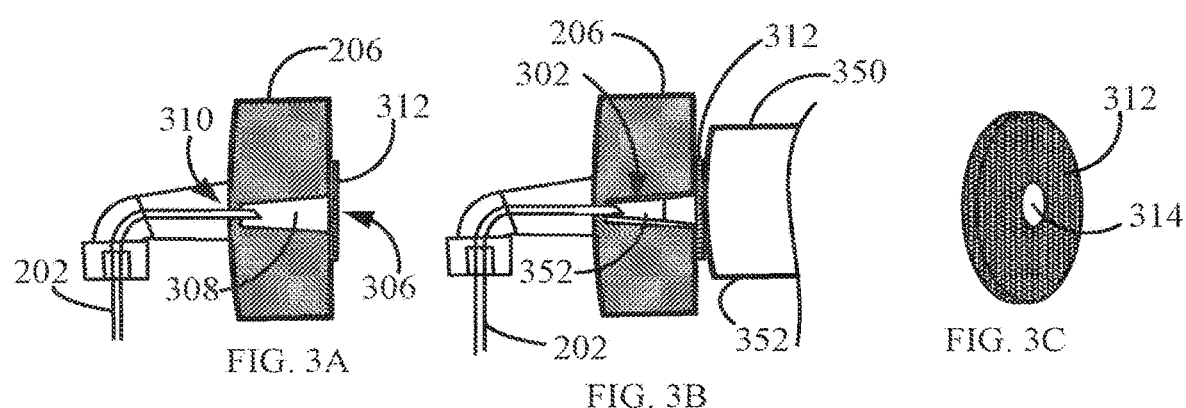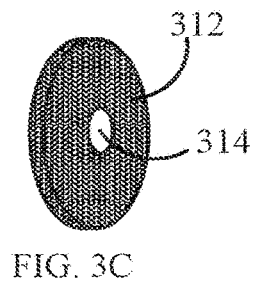
FIG. 3A  FIG. 3B  FIG. 3C
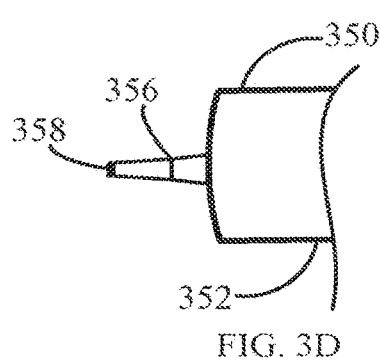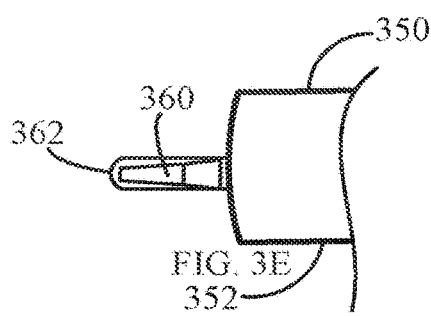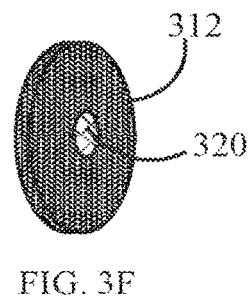
FIG. 3D  FIG. 3E  FIG. 3F
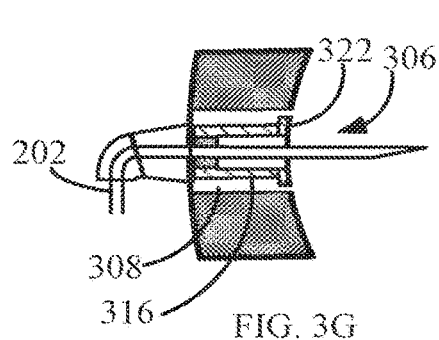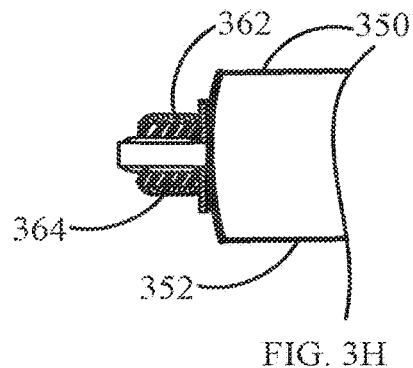
FIG. 3G  FIG. 3H
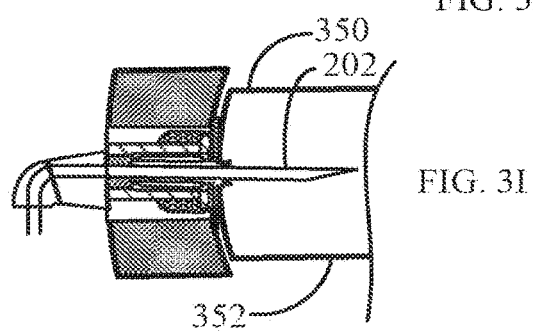
FIG. 3I

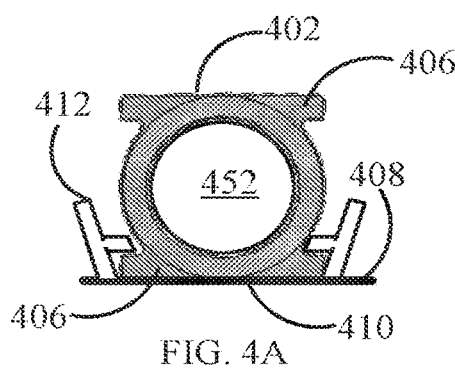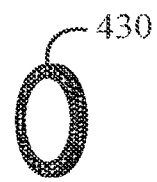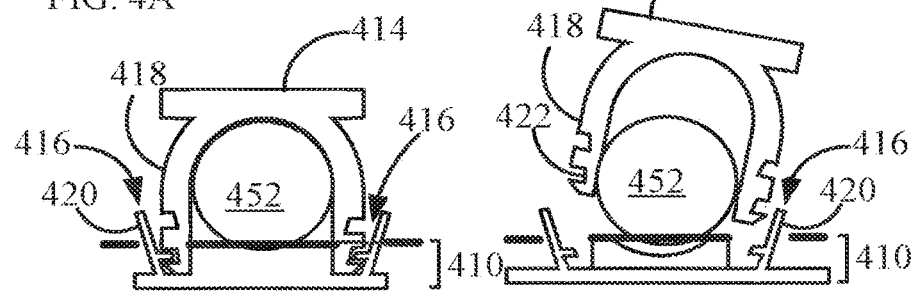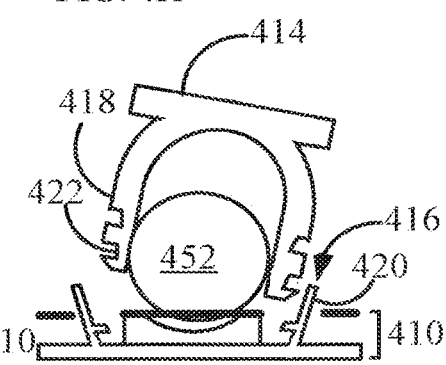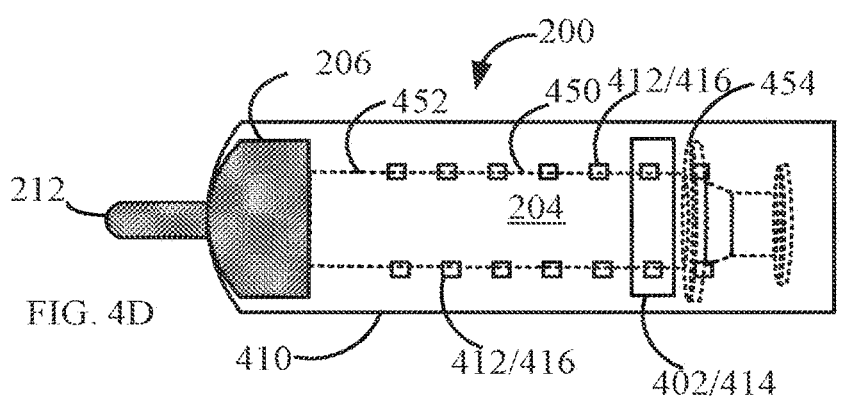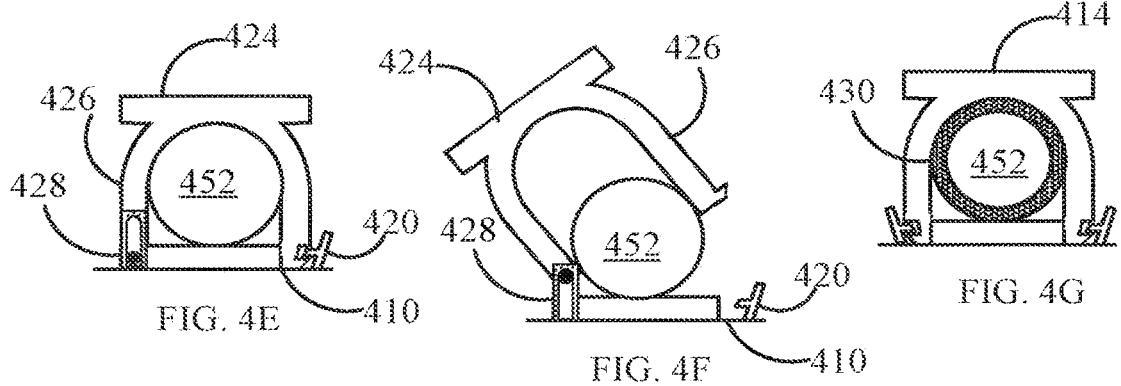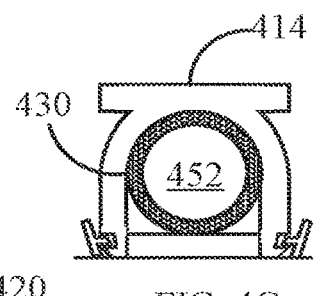

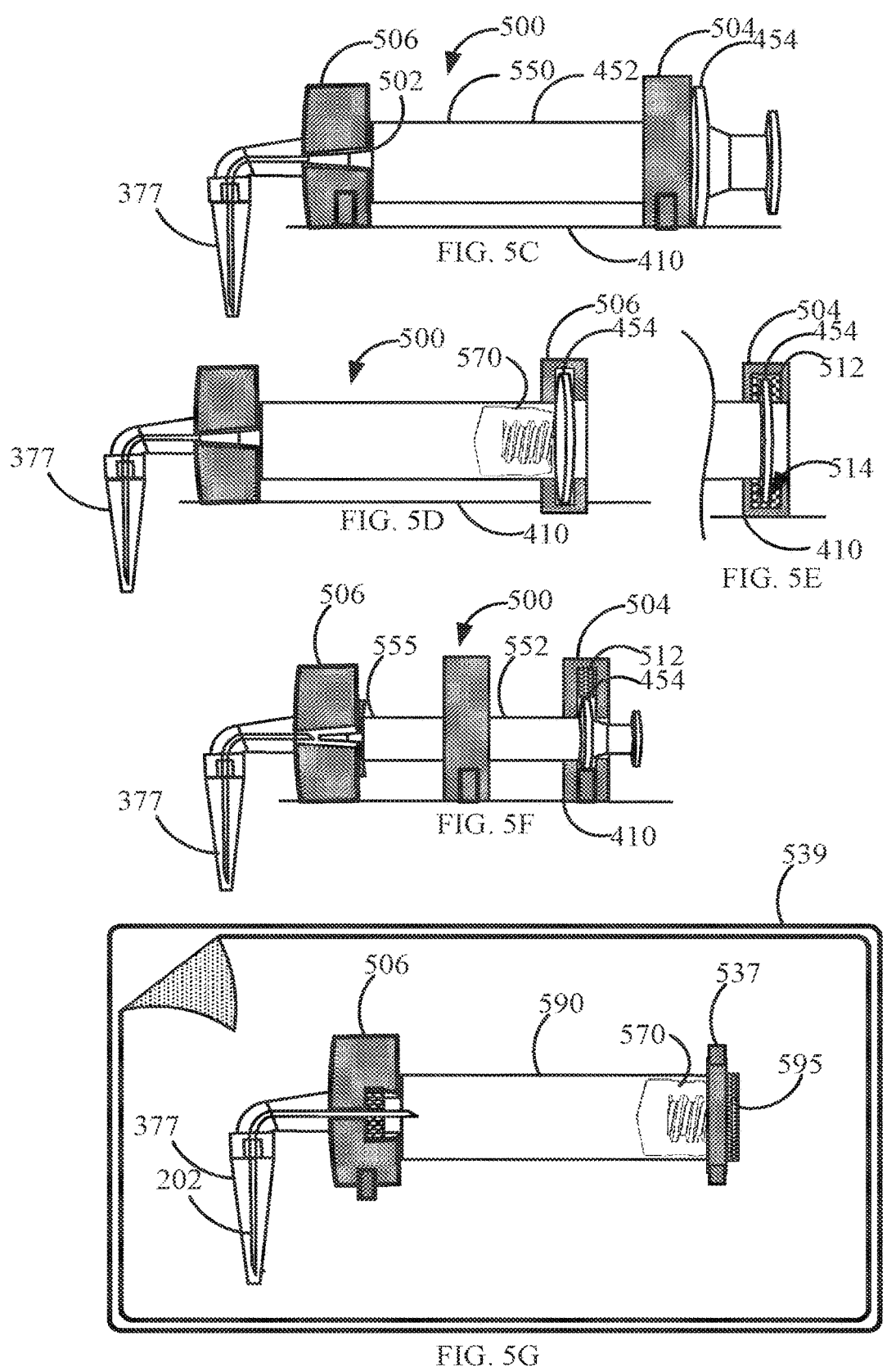

BENT FLUID PATH ADD ON TO A PREFILLED FLUID RESERVOIR

CROSS REFERENCE TO RELATED APPLICATION

This application is continuation of U.S. patent application Ser. No. 17/395,670, filed Aug. 6, 2021, and published as U.S. Patent App. Pun. No. 2021/0361871, which is a divisional of U.S. patent application Ser. No. 15/766,719, filed Apr. 6, 2018, and issued as U.S. Pat. No. 11,116,908, which is a section 371 of International Application No. PCT/US2016/56213, filed Oct. 10, 2016, and published as International Publication No. WO 2017/062931, which is a continuation of U.S. patent application Ser. No. 15/204,542, filed Jul. 7, 2016, and issued as U.S. Pat. No. 10,576,207, which claims the benefit of U.S. Provisional Patent App. No. 62/281,536, filed Jan. 21, 2016 and U.S. Provisional Patent App. No. 62/284,806, filed Oct. 9, 2015, the disclosures of which are incorporated herein by reference.

FIELD AND BACKGROUND OF THE INVENTION

The present invention, in some embodiments thereof, relates to a self-injector and, more particularly, but not exclusively, to a patch self-injector.

A subcutaneous (SC) injection is a method of administering medication under the skin, commonly into fatty tissue between the skin and the muscle. The current trend toward subcutaneous injection for biologicals using auto-injectors such as, for example, reusable and disposable pens, auto-injectors, and patch injectors that adhere to the surface of the skin gives users the freedom to self-inject at home.

In many cases, reformulated drugs can be more concentrated, at times more viscous and the desired injection volume greater than 1 mL. For high viscosity products, delivery in under 10 seconds can lead to painful injections, which may result in users failing to follow their treatment regimen. It may be difficult at times for a user to keep a Pen or any other upright injector stationary and at a correct angle of injection during injections for periods of over 10 seconds or several minutes. Patch auto or self-injectors for self-administered SC injections are therefore becoming more common.

Additional background art includes U.S. Pat. Nos. 6,843,782 and 5,858,001.

SUMMARY OF THE INVENTION

According to an aspect of some embodiments of the present invention there is provided an add-on for a self-injector including an adaptor including at least one coupling sized and shaped to couple the adaptor to a fluid reservoir, a bent fluid path configured at a first end to penetrate tissue and coupled at a second end to the adaptor and wherein the add-on coupled to the fluid reservoir forms an integral self-injector cartridge unit configured to be sterilized and filled with an injectable.

According to some embodiments of the invention, the add-on includes a needle protective cap. According to some embodiments the fluid path is bent at a 90-degree angle. According to some embodiments, the add-on further includes at least one fastener sized and fitted to couple the body of the reservoir to a self-injector.

According to an aspect of some embodiments of the present invention there is provided an add-on for a self-injector including an adaptor including at least one coupling sized and shaped to couple the adaptor to a fluid reservoir, a bent fluid path configured at a first end to penetrate tissue and coupled at a second end to the adaptor and wherein when the add-on is coupled to the fluid reservoir sterile fluid communication is secured between the reservoir and the first end of the bent fluid path. According to some embodiments of the invention, the bent fluid path includes a coupling at the second end sized and shaped to couple the bent fluid path to the adaptor and secure sterile fluid communication in-between. According to some embodiments of the invention, the add-on further includes at least one fastener sized and fitted to couple the body of the reservoir to a self-injector. According to some embodiments of the invention, the bent fluid path includes a hollow needle. According to some embodiments of the invention, the fluid path is bent at a 90-degree angle.

According to some embodiments of the invention, the reservoir is a prefilled cartridge. According to some embodiments of the invention, the reservoir is a syringe. According to some embodiments of the invention, the reservoir is a vial. According to some embodiments of the invention, at least a portion of the reservoir is made of glass. According to some embodiments of the invention, at least a portion of the reservoir is made of a plastic material. According to some embodiments of the invention, the add-on is sterilizable en bloc. According to some embodiments of the invention, the adaptor coupling is a Leur lock coupling. According to some embodiments of the invention, the adaptor coupling is a vial adaptor. According to some embodiments of the invention, the adaptor coupling is a slide-on fluid reservoir coupling. According to some embodiments of the invention, the adaptor further includes a coupling sized and shaped to couple the add-on to a self-injector.

According to an aspect of some embodiments of the present invention there is provided an add-on for a self-injector, including at least one adaptor including at least one bent fluid path and sized and fitted to sterilely couple the bent fluid path to at least a tip of a fluid reservoir, and at least one fastener sized and fitted to a body of the fluid reservoir to the self-injector, and wherein the adaptor and the fastener are configured to couple to the self-injector at least one of a plurality of reservoirs having different sizes and tip types.

According to some embodiments of the invention, the distance between the adaptor and the fastener is adjustable. According to some embodiments of the invention, the internal diameter of the fastener is adjustable. According to some embodiments of the invention, the add-on further includes a fitting sized and shaped to fit along the inner circumference of the fastener. According to some embodiments of the invention, the fitting reduces the inner diameter of the fastener. According to some embodiments of the invention, at least a portion of the fastener is made of a plastic material. According to some embodiments of the invention, at least a portion of the fluid reservoir is made of glass. According to some embodiments of the invention, at least a portion of the fluid reservoir is made of a plastic material. According to some embodiments of the invention, the bent fluid path includes a hollow needle. According to some embodiments of the invention, the fluid path is bent at a 90-degree angle.

According to some embodiments of the invention, the reservoir is a prefilled cartridge. According to some embodiments of the invention, the reservoir is a fluid reservoir. According to some embodiments of the invention, the reservoir is a vial. According to some embodiments of the invention, add-on is sterilizable en bloc. According to some embodiments of the invention, the adaptor coupling is a Leur lock coupling. According to some embodiments of the invention, the adaptor coupling is a vial adaptor. According to some embodiments of the invention, the adaptor coupling is a slide-on fluid reservoir coupling. According to some embodiments of the invention, the adaptor further includes a coupling sized and shaped to couple the add-on to a self-injector.

According to an aspect of some embodiments of the present invention there is provided an add-on to a self-injector coupling system, including a self-injector including a support plate with a plurality of attachment points, at least one adaptor including at least one bent fluid path and sized and fitted to sterilely couple the bent fluid path to at least a tip of a fluid reservoir and at least one fastener sized and fitted to couple to a body of the fluid reservoir and to at least one of the attachment points.

According to some embodiments of the invention, the adaptor is sized and fitted to couple to at least one of the attachment points. According to some embodiments of the invention, the attachment points are distributed on the support plate at varying distances from the adaptor. According to some embodiments of the invention, the varying distances correspond to varying lengths of the fluid reservoir. According to some embodiments of the invention, the internal diameter of the fastener is adjustable. According to some embodiments of the invention, the system further includes a fitting sized and shaped to fit along the inner circumference of the fastener. According to some embodiments of the invention, the fitting reduces the inner diameter of the fastener.

According to an aspect of some embodiments of the present invention there is provided a self-injector kit, including at least one self-injector including a support plate with a plurality of attachment points, a plurality of adaptors including at least one bent fluid path and sized and fitted to sterilely couple the bent fluid path to at least a tip of at least one type of fluid reservoir and a plurality of fasteners sized and fitted to couple to at least one diameter of a body of the fluid reservoir and to at least one of the attachment points.

According to some embodiments of the invention, at least one fitting is sized and shaped to fit along the inner circumference of at least one of the plurality of fasteners. According to some embodiments of the invention, the fitting reduces the inner diameter of the fastener. According to some embodiments of the invention, the fluid reservoir is at least one of a prefilled cartridge, a syringe and a vial. According to some embodiments of the invention, at least a portion of the fluid reservoir is made of glass. According to some embodiments of the invention, at least a portion of the fastener is made of a plastic material. According to some embodiments of the invention, at least one of the adaptors is sterile.

According to an aspect of some embodiments of the present invention there is provided a method of assembling an add-on for a self-injector including: selecting an empty fluid reservoir, forming a self-injector cartridge unit by coupling at least a tip of the fluid reservoir to an adaptor including at least one bent fluid path and sized and fitted to fluidly couple the bent fluid path to at least a tip of the fluid reservoir and establishing fluid communication between the fluid reservoir and the bent fluid path.

According to some embodiments of the invention, the method further includes sterilizing the cartridge, filling the fluid reservoir with a sterile injectable, inserting a plunger into a non-bent fluid path end of the fluid reservoir and sterilely sealing the end of the fluid reservoir. According to some embodiments of the invention, the method further includes selecting at least one fastener and coupling the fastener to a body of the fluid reservoir and coupling the fastener to at least one corresponding attachment point on the injector.

According to an aspect of some embodiments of the present invention there is provided a method of coupling an add-on for a self-injector to a fluid reservoir including: selecting a fluid reservoir, coupling at least a tip of the fluid reservoir to an adaptor including at least one bent fluid path and sized and fitted to fluidly couple the bent fluid path to at least a tip of the fluid reservoir and establishing sterile communication between the fluid reservoir and the bent fluid path.

According to some embodiments of the invention, the method further includes selecting at least one fastener and coupling the fastener to a body of the fluid reservoir and coupling the fastener to at least one corresponding attachment point on the injector.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A-4H are plan and perspective view simplified illustration of exemplary embodiments of a modular fluid reservoir-injector coupling system;

FIGS. 5A, 5B, 5C, 5D, 5E, 5F and 5G are part sectional side view simplified illustrations of positioning of fasteners coupling a fluid reservoir to a self-injector.

DESCRIPTION OF SPECIFIC EMBODIMENTS OF THE INVENTION

Figure 1:
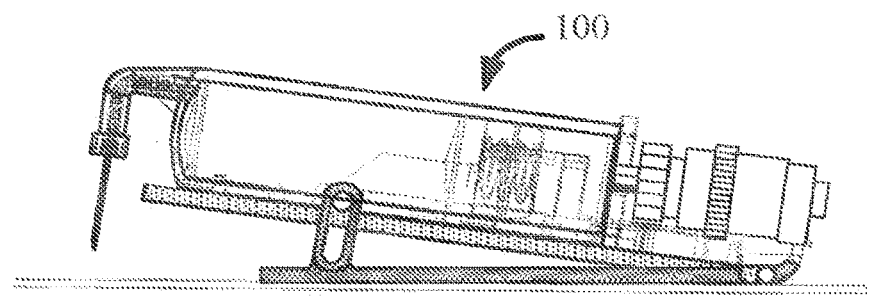
FIG. 1 is a side view simplified illustration of a patch type self-injector.

The present invention, in some embodiments thereof, relates to self-injectors and, more particularly, but not exclusively, to a patch self-injector.

An aspect of some embodiments of the invention relates to a self-injector sized and fitted to couple fluid reservoirs of variable sizes and tip types to the injector. In some embodiments, the self-injector comprises at least a needle-bearing portion and at least one fastener attachable to the injector and at least to a barrel of a fluid reservoir. In some embodiments, the needle bearing portion comprises a needle protective cap. In some embodiments, the self-injector and the fluid reservoir are provided sterile. For example, the reservoir, needle bearing portion and cap may be assembled and sterilized together. In some embodiments, the self-injector and the fluid reservoir are provided unsterile. In some embodiments, the self-injector and the fluid reservoir are sterilized prior to filling with an injectable. In some embodiments, post sterilization the sterile fluid reservoir is filled with an injectable and provided sterilely sealed and capped with a protective cap. In some embodiments, the distance between the needle-bearing portion and the fastener is adjustable. In some embodiments, the internal radius of the fastener is adjustable. In some embodiments, the injector comprises a patch type self-injector. In some embodiments, the injector comprises a bent needle. In some embodiments, the needle is bent at a 90-degree angle. In some embodiments, at least one portion of the injector comprises at least a bore sized and fitted to accommodate a fluid reservoir tip. In some embodiments, at least a portion of the needle extends through the bore. In some embodiments, the needle-bearing portion is fixed in place. In some embodiments the fluid reservoir comprises a syringe. In some embodiments, the fluid reservoir comprises a vial. In some embodiments the fluid reservoir comprises a prefilled cartridge.

In some embodiments, the self-injector is sized and fitted to accommodate refillable fluid reservoirs. In some embodiments, a self-injector is sized and fitted to accommodate prefilled fluid reservoirs. In some embodiments the prefilled fluid reservoir tips are sealed for sterility. In some embodiments, the injector comprises one or more adaptors that couple the needle to one or more fluid reservoir tip types. In some embodiments, the adaptor is sized and fitted for coupling the needle to a slip or push-on type fluid reservoir tip. In some embodiments, the adaptor is sized and fitted for coupling the needle to a Luer-lock type fluid reservoir tip. In some embodiments, the adaptor is sized and fitted for coupling the needle to a catheter type fluid reservoir tip. In some embodiments, the adaptor is sized and fitted for coupling the needle to a fluid reservoir with a centered tip. In some embodiments, the adaptor is sized and fitted for coupling the needle to a fluid reservoir with an eccentric tip.

An aspect of some embodiments of the invention relates to a self-injector comprising a modular fluid reservoir-injector coupling system. In some embodiments, the modular system comprises a support plate sized and fitted to accommodate variable types and sizes of fluid reservoirs. In some embodiments, the injector comprises a bent needle. In some embodiments, the needle is bent at a 90-degree angle. In some embodiments, the support plater comprises one or more notches configured to accommodate fasteners that fix the fluid reservoir to the injector. In some embodiments, at least a portion of one or more fasteners is fixedly coupled to a self-injector support plate. In some embodiments, at least a portion of one or more fasteners is releasably coupled to the self-injector support plate. In some embodiments, one or more fasteners comprises at least an aperture sized and fitted to accommodate a fluid reservoir tip. In some embodiments, at least one fastener comprises a bent needle. In some embodiments, at least one fastener comprises at least a bore sized and fitted to accommodate a fluid reservoir tip. In some embodiments, at least a portion of the needle extends through the aperture or bore.

In some embodiments, at least one fastener comprises a latch and a hinge. In some embodiments, at least one fastener comprises one or more latches. In some embodiments, at least one fastener is sized and fitted to fasten a barrel of a fluid reservoir. In some embodiments, at least one fastener is sized and fitted to fasten a finger flange of a fluid reservoir. In some embodiments, at least one fastener comprises at least one fitting sized and fitted for a specific fluid reservoir barrel diameter. In some embodiments, at least one fastener is fitted with an at least partially resilient pad. In some embodiments, at least a portion of a fluid reservoir is urged against the resilient pad when locked into place in the injector. In some embodiments, the resilient pad stops leaks from the fluid reservoir tip-needle coupling. In some embodiments, the resilient pad comprises an aperture for a tip of a needle.

An aspect of some embodiments of the invention relates to a self-injector comprising a bent needle and having a Luer-lock coupling sized and fitted to receive a fluid reservoir with a male Luer-lock type tip. In some embodiments, the Luer-lock coupling comprises a cylinder coupled at one end to the injector and comprising a tabbed rim configured to screw into a male Luer-lock fluid reservoir tip. In some embodiments, at least a portion of the bent needle is disposed in a lumen of the cylinder. In some embodiments, at least a portion of the needle is attached to the inside wall of the cylinder. In some embodiments, at least a portion of the cylinder lumen between the portion of the needle and the inside wall comprises a seal. In some embodiments, at least one end of the bent needle extends beyond the cylinder tabbed rim. In some embodiments, the end of the bent needle extending beyond the cylinder tabbed rim comprises a protective sheath. In some embodiments, the protective sheath maintains sterility of the needle end. In some embodiments, the protective sheath maintains sterility of the portion of the needle inside the cylinder lumen up to and including the end of the needle extending beyond the tabbed rim. In some embodiments, upon coupling, the rim of the male luer lock urges the protective sheath against the tip of the needle. In some embodiments, the needle tip ruptures the protective sheath urged against the needle tip by the male Luer lock rim.

An aspect of some embodiments of the invention relates to a self-injector sized and fitted to sterilely accommodate variable types and sizes of fluid reservoirs. In some embodiments, the self-injector comprises a coupling that maintains sterility of a pathway of an injectable during and after coupling to a fluid reservoir containing the injectable. In some embodiments, the injector coupling comprises an end of a needle at least partially isolated by at least one protective sheath. In some embodiments, during coupling a tip of a coupled fluid reservoir urges at least one sheath against the needle end rupturing the protective sheath. In some embodiments, a tip of a coupled fluid reservoir comprises a sealing membrane over an opening in the tip. In some embodiments, during coupling the injector needle is urged against the membrane and penetrates the fluid reservoir tip.

An aspect of some embodiments of the invention relates to a self-injector kit comprising a support plate and a plurality of fasteners and fittings sized and fitted to attach to the support plate. In some embodiments, the plurality of fasteners and fittings sized and fitted to sterilely accommodate variable types and sizes of fluid reservoirs. In some embodiments, the plurality of fasteners comprises quick attachment type coupling. In some embodiments, the plurality of fasteners comprises at least one one-click type coupling. In some embodiments, various fasteners can be coupled to the support place at various desired locations. In some embodiments, at least one fastener comprises a bent needle. In some embodiments, one or more fasteners are configured to accommodate at least one fitting. In some embodiments, one or more fasteners and/or fittings comprise one or more apertures at various internal diameters to fit at least one barrel and/or finger flange of at least one fluid reservoir.

An aspect of some embodiments of the invention relates to a method of loading variable types and sizes of fluid reservoirs a self-injector. In some embodiments, the method comprises one or more fasteners sized and fitted for a barrel and finger flange of a selected fluid reservoir. In some embodiments, the method comprises optionally, selecting at least one fitting sized and fitted for a barrel and finger flange of a selected fluid reservoir. In some embodiments, the method further comprises optionally sliding or coupling one or more fittings onto the barrel or finger flange of the fluid reservoir. In some embodiments, the method further comprises sliding or coupling one or more fasteners onto the barrel or finger flange of the fluid reservoir. In some embodiments, the method further comprises inserting a tip of a fluid reservoir into an aperture in a needle portion of the injector. In some embodiments, the method further comprises optionally inserting a tip of a fluid reservoir into an aperture in a needle-bearing fastener. In some embodiments, the method further comprises coupling the fasteners to a support plate. In some embodiments, the method further comprises connecting the fluid reservoir to an injector fluid reservoir plunger driving system.

Introduction

Reference is now made to FIG. 1, which is a side view simplified illustration of a patch type self-injector as described in U.S. Provisional Patent Application 62/284,806 and is hereby incorporated in its entirety. Self-injector 100 comprises a bent needle 102, e.g., bent at a 90-degree angle coupled to a cartridge 104. Cartridge 104 may be pre-filled with an injectable. Cartridge 104 may be mounted on a support plate 106 and include a plunger 108 driven by electric motor driving gear 110. Following an injection procedure, cartridge 104 may be disposed of and replaced by a new pre-filled cartridge.

The injector powertrain and plunger driving systems are explained in detail in the above referenced U.S. Provisional Patent Application 62/284,806 and will therefore not be repeated herein.

Optional Components of a Modular Self-Injector-Fluid Reservoir Coupling System.

Figure 2A:
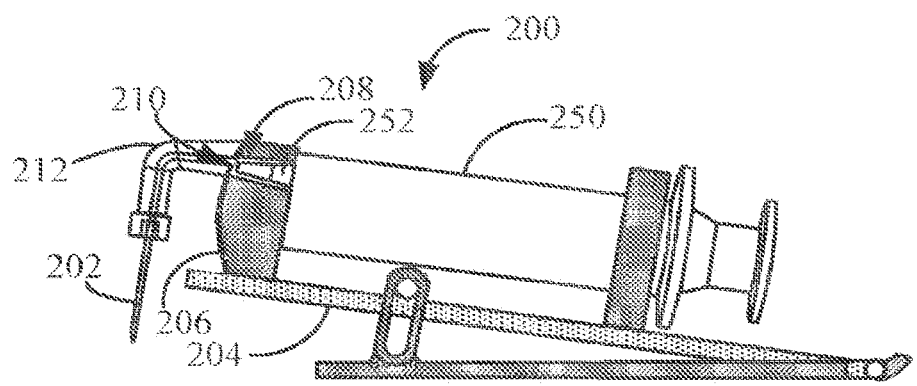
FIGS. 2A and 2B are side view simplified illustrations of optional exemplary embodiments of a modular patch type self-injector.
Figure 2B:
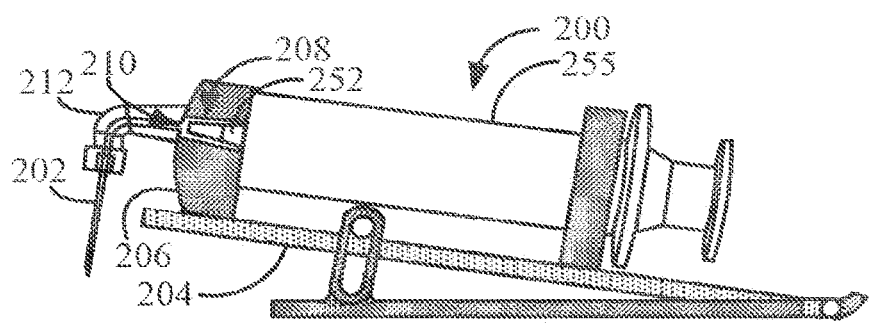

Reference is now made to FIGS. 2A, 2B and 2C, collectively referred to as FIG. 2, which are side view simplified illustrations of optional exemplary embodiments of a modular patch type self-injector. As shown in FIG. 2, a self-injector 200 may be sized and fitted to accommodate variable types and sizes of fluid reservoirs. As in the example of FIG. 1, in some embodiments, auto-injector 200 comprises a bent needle 202, e.g., bent at a 90-degree angle. As explained in greater detail elsewhere in the disclosure, in some embodiments, self-injector 200 comprises a support plate 204 and at least a needle 202-bearing portion 206. In some embodiments, needle-bearing portion 206 comprises at least a bore 208 sized and fitted to accommodate a fluid reservoir 250/255 tip 252. In some embodiments, bore 208 comprises an aperture 210 leading to the bent portion 212 of needle 202. In some embodiments, at least a portion of needle 202 sealingly extends through aperture 210 and into bore 208. In some embodiments, needle-bearing portion 206 is fixed on support plate 204.

In some embodiments, shown in FIG. 2A, bore 208 is disposed eccentrically within needle-bearing portion 206 to accommodate an eccentric tip fluid reservoir. In some embodiments, shown in FIG. 2B, bore 208 is disposed centrally within needle-bearing portion 206 to accommodate a regular (central) tip fluid reservoir.

Optional Examples of Injector-Fluid Reservoir Couplings

Commonly used fluid reservoir tips include slip or push on tips and Luer lock type tips. Plastic fluid reservoirs comprise plastic tips of both types whereas glass fluid reservoir tips are commonly made of metal. Some glass fluid reservoirs comprise glass slip-on type tips. The commonly used fluid reservoir-needle coupling practice attempts to maintain a sterile injectable passageway however this may be challenging at times. The common practice is to store both fluid reservoirs and needles each in a sterile pouch to limit their exposure time to the environment from the moment of removal from the pouch until the moment of injection. This practice is not practical when it comes to self-injectors and especially patch-type self-injectors.

Slip/Push-on Type

Figure 3J:
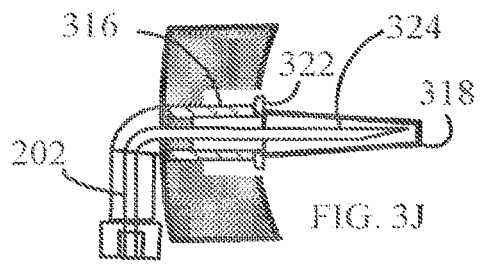
FIGS. 3A-3P are cross-section section and perspective view simplified illustrations of exemplary embodiments of injector-fluid reservoir couplings.
Figure 3L:
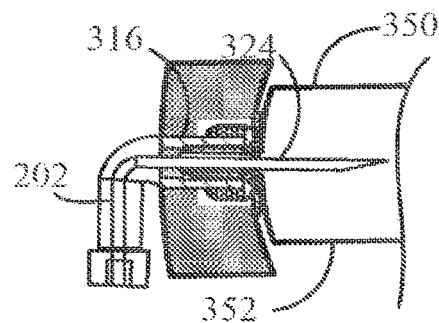
Figure 3K:
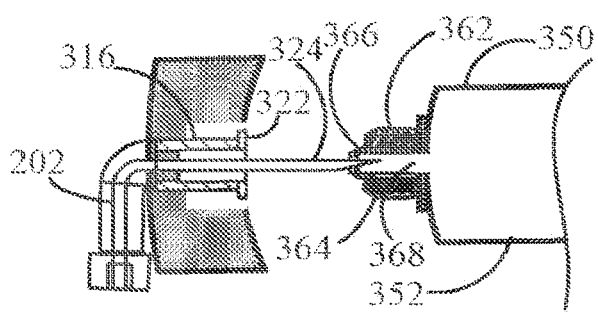
Figure 3M:
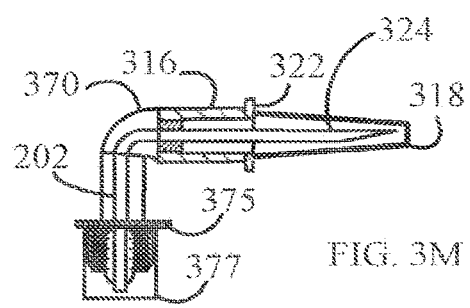
Figure 3N:
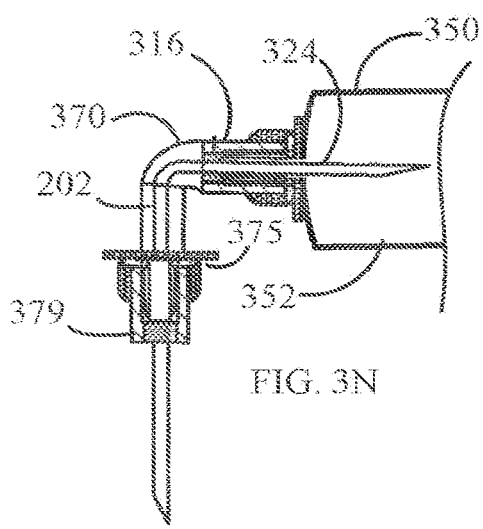
Figure 3O:
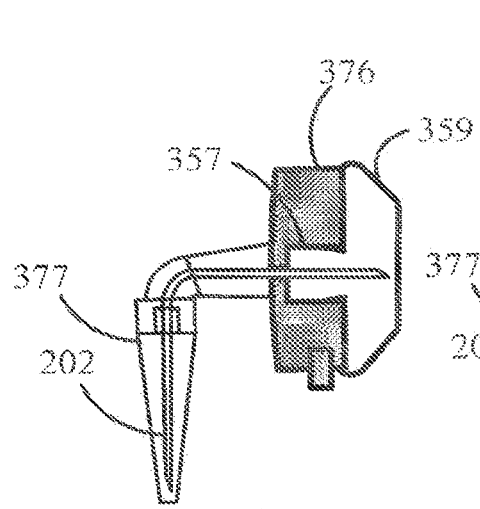
Figure 3P:
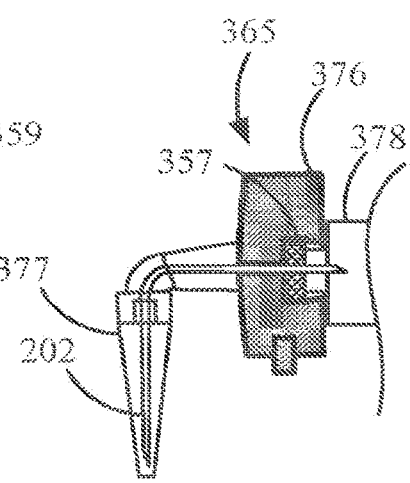

Reference is now made to FIGS. 3A-3P, collectively referred to as FIG. 3, which are cross-section section and perspective view simplified illustrations of exemplary embodiments of injector-fluid reservoir couplings. The exemplary embodiments of FIGS. 3A-3L depict one or more adaptors that couple needle 202 to one or more various fluid reservoir tip types. For example, FIG. 3A, illustrates needle-bearing portion 206 comprising an adaptor 302 sized and fitted for coupling needle 202 to a slip or push-on type fluid reservoir tip 352. A centrally disposed bore 308 opens on one side to an opening 306 facing a fluid reservoir to receive a fluid reservoir tip and ends on the opposite side at an aperture 310 on the opposite side sized to sealingly accommodate at least a portion of needle 202. Optionally, in some embodiments, bore 308 comprises cone geometry. In some embodiments, bore 308 comprises cylinder geometry. Optionally and as also shown in FIG. 3C, in some embodiments, needle-bearing portion 206 may further comprise a resilient fitting 312 attached adhesively or by any other suitable method over opening 306. In some embodiments, fitting 312 may comprise an aperture 314 sized to accommodate a correspondingly sized slide-on type fluid reservoir tip. In some embodiments, when at least a portion of a fluid reservoir 350 is urged against the resilient fitting when locked into place in the injector, resilient fitting 312 stops possible leaks from the fluid reservoir tip-needle coupling.

In some embodiments, fitting 312 may be made of a resilient type suitable material, e.g., Silicone to act as a seal and seal opening 306 when a fluid reservoir barrel 352 is urged against needle-bearing portion 206 as shown in FIG. 3B.

As illustrated in FIGS. 3A and 3B, in some embodiments, end of needle 316 may at least partially extend into bore 308 and into a lumen of a fluid reservoir tip 354 when a fluid reservoir 350 is coupled to the self-injector. As shown in FIGS. 3D and 3E, tips of a fluid reservoir 350 may be sealed for sterility. For example, an opening of a fluid reservoir tip 356 (FIG. 3D) may be sealed by a membrane 358, or, alternatively, a fluid reservoir tip 360 (FIG. 3E) may be covered by a protective sheath 362. In some embodiments, when coupled to a fluid reservoir 350, end 316 of needle 202 extending into bore 308 is configured to break most types of fluid reservoir tip seals protecting sterility of the injectable inside fluid reservoir 350. Ion some embodiments, and shown in FIG. 3F, fitting 312 aperture 314 may be sealed by a membranous seal 320. In some embodiments, when self-injector 200 is coupled to a fluid reservoir 350, a tip 356/360 of fluid reservoir 350 may break membranous seal 320.

Luer-Lock Type

Referring now to FIGS. 3G-3I which illustrate self-injector 200 comprising bent needle 202 and Luer-lock coupling 316 sized and fitted to receive a fluid reservoir 350 with a male Luer-lock type tip 362. In some embodiments, Luer-lock coupling 316 comprises a cylinder sealingly coupled at one end to needle 202 and injector 200 and comprising a tabbed rim 322 on the opposite end that opens toward bore 308 opening 306. In some embodiments, tabbed rim 322 is configured to thread into a sleeve 364 on a male Leur-lock fluid reservoir tip 362. FIG. 3I shows Luer-lock coupling 316 and Luer-lock type fluid reservoir 350 tip 362 in a fully mated configuration.

The exemplary embodiment depicted in FIGS. 3J-3L illustrates a Luer lock coupling system similar to that described elsewhere in the disclosure. Optionally, in some embodiments and as shown in FIG. 3J, end 324 of bent needle 202 extending beyond Luer-lock coupling 316 tabbed rim 322 comprises a protective sheath 318 configured to maintain sterility needle end 324. In some embodiments, protective sheath 318 is made of a pliable membranous material e.g., rubber, polyurethane or any other suitable material. In some embodiments, when mated as shown in FIG. 3K, a rim 366 of male Luer lock fluid reservoir 350 tip 362 urges protective sheath 318 against needle end 324. In some embodiments and as shown in FIG. 3K, needle end 324 breaks protective sheath 318 as it enters into the lumen 368 of fluid reservoir Luer lock tip 362. FIG. 3L shows Luer-lock coupling 316 and Luer-lock type fluid reservoir 350 tip 362 in a fully mated configuration. Additionally and optionally, in some embodiments, fluid reservoir male Luer lock tip 316 comprises a seal similar to seal 358 of fluid reservoir tip 356.

In some embodiments and as shown in FIGS. 3M and 3N, self-injector may comprise a bent needle adaptor 370 comprising a fluid reservoir coupling similar to the examples described elsewhere in the disclosure and a second coupling 375 at a second end of the adaptor 370. In the example depicted ion FIGS. 3M and 3N second coupling 375 comprises a Leur lock tip. A cover 377 protects second coupling 375 from the environment and maintains the sterility of needle adaptor 370. In some embodiments, adaptor 370 provides the freedom to couple a standard needle 379 to self-injector 200. In the exemplary embodiment shown in FIG. 3N, protective cap 377 has been removed and a Leur lock tip needle 379 is coupled to needle adaptor 370 and fluid reservoir 350.

As shown in FIGS. 3O and 3P, an exemplary embodiment of bent needle adaptor 376 comprises a vial adaptor 357 such as, for example a Medimop Medical Projects Ltd. vial adaptor described in U.S. Pat. No. 7,326,194. In some embodiments, bent needle adaptor 376 comprises a sterile cover 359. In some embodiments, bent needle adaptor 376 comprises needle cap 377. Optionally and alternatively and as shown in FIG. 3P, bent needle adaptor 376 may be attached to an empty vial 378 to form a single non-sterile self-injector cartridge unit 365. In some embodiments, cartridge unit 365 can then be sterilized and filled with an injectable.

Optional Examples of Fasteners and Fittings

An aspect of some embodiments of the invention relates to a self-injector comprising a modular fluid reservoir-injector coupling system. Self-injectors and specifically patch self-injectors are designed to avoid movement of the injection needle in the tissue during the injection process and thus to minimize pain associated with the injection. This is achieved by various coupling methods that fixedly attach the injection needle and/or the fluid reservoir cartridge to the self-injector housing.

Reference is now made to FIGS. 4A-4H, collectively referred to as FIG. 4, which are plan and perspective view simplified illustration of exemplary embodiments of a modular fluid reservoir-injector coupling system. In the examples depicted in FIG. 4, self-injector 200 comprises one or more fasteners 402, sized and fitted to accommodate at least a barrel 452 or a finger flange 454 of a fluid reservoir 450. In some embodiments and as shown in FIGS. 4A and 4B, injector 200 comprises one or more fasteners configured to couple variable types and sizes of fluid reservoirs to self-injector 200. As shown in FIG. 4A, in some embodiments, a fastener 404 comprises ring geometry sized and fitted to slide onto a fluid reservoir barrel of a corresponding diameter. In some embodiments, fastener 404 further comprises at least one protrusion 406 extending from the periphery of fastener 404. In the exemplary embodiment depicted in FIG. 4A protrusion 406 extends tangentially from the ring of fastener 404, however protrusion 406 may extend radially or in any other suitable geometric configuration. In some embodiments, protrusion 406 is oriented parallel at least to a surface 408 of a support plate 410. In the exemplary embodiment illustrated in FIG. 4A, at least one protrusion 406 is fixedly coupled to the support plate 410 by at least one retention member. In the example shown in FIG. 4A, the attachment member comprises a retention cantilever 412. In some embodiments, retention lever 412 are elastic and/or comprise at least an elastic coupling to support plate 410. However, the attachment member may comprise any type of suitable attachment mechanism. In some embodiments, retention cantilever 412 is configured to releasably couple fastener 404 protrusion 406 to support plate. FIGS. 4B and 4C illustrate an exemplary embodiment in which fastener 414 comprises an inverted U geometry. In some embodiments, support plate 410 a plurality of notches 416 configured to accommodate legs 418 of fastener 414. In some embodiments, support plate 410 notches 416 comprise retention cantilevers 420 configured to releasably couple fastener 414 to support plate by fitting into one or more corresponding recesses 422 in legs 418. Optionally, a plurality of recesses 422 supports adjustment of the internal radius of fastener 414 by adjusting the depth of insertion of fastener 414 one or more legs 418 into support plate 410. Thus, a plurality of recesses 422 renders fastener 414 to be configured to size and fit a variety of fluid reservoir sizes.

As shown in FIG. 4D, in some embodiments, support plate 410 comprises a plurality of attachment points 412/416 distributed in a fashion that allows fasteners 402/414/424 to be coupled to support plate 410 at varying distances from needle portion 206 to accommodate fluid reservoirs of varying lengths. In some embodiments, attachment points 412/416 optionally comprise cantilevers 420 of the type shown in FIG. 4A. In some embodiments, attachment points 412/416 optionally comprise notches 416 and retention cantilevers 420 configured to releasably couple fasteners of the type depicted in FIGS. 4B and 4C. In some embodiments, attachment points 412/416 optionally comprise sliding hinges and retention levers in a configuration shown in FIGS. 4E and 4F. Additionally and optionally, attachment points 412/416 may comprise any similar suitable attachment mechanism other than the exemplary embodiments described herein.

FIGS. 4E and 4F illustrate an exemplary embodiment in which fastener 424 comprises a hinged inverted U geometry.

In the example in FIGS. 4E and 4F one leg 426 comprises a sliding hinge 428 configured to form a large gap when open to release or receive a fluid reservoir barrel 452. In the closed configuration shown in FIG. 4E, fastener 424 non-hinged leg 426 is locked in place by a retention cantilever 420.

In some embodiments, at least one of fasteners 402/414/424 comprises the same size to fit onto the same support plate 410. In some embodiments and as shown in FIGS. 4G and 4H, fasteners 402/414/424 are fitted with one or more ring geometry fittings 430 (FIG. 4H) at various diameters sized and fitted to a corresponding diameter of a specific fluid reservoir barrel. In some embodiments, fittings 430 are configured to slide onto a barrel 452 of a fluid reservoir 450 and provide sufficient friction when a fastener, e.g., fasteners 414/424 is in the closed configuration to prevent axial slippage and movement of fluid reservoir barrel 452 in respect to support plate 410.

FIGS. 4G and 4H depict a fastener of the type illustrated in FIGS. 4B and 4C, however fittings 430 may be fitted in any one of the fasteners described herein or any other similar type of fastener.

Optional Examples of Adaptor-Fluid Reservoir Couplings and Fasteners Positioning In order to secure fixed coupling of a fluid reservoir to a self-injector, fasteners such as fasteners 420/414/424 need to be adjusted to a length of a fluid reservoir barrel in addition to fixing the fluid reservoir to a surface such as support plate 410. In most cases this can be achieved by sliding the fastener along the fluid reservoir barrel as described elsewhere in the disclosure and/or couple a fastener to a finger flange of the fluid reservoir. The structure of modular support plate 410 described elsewhere in the disclosure allows for positioning a fastener at almost any desired location when fitted to a fluid reservoir barrel or finger flange. Reference is now made to FIGS. 5A-5G, which are part sectional side view simplified illustrations of positioning of fasteners coupling a fluid reservoir to a self-injector.

Figure 5A:
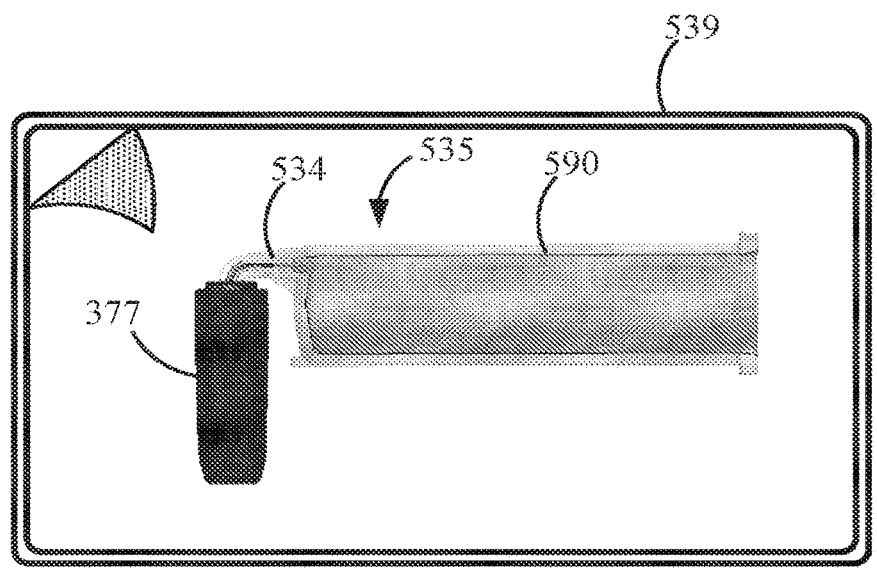
Figure 5B:
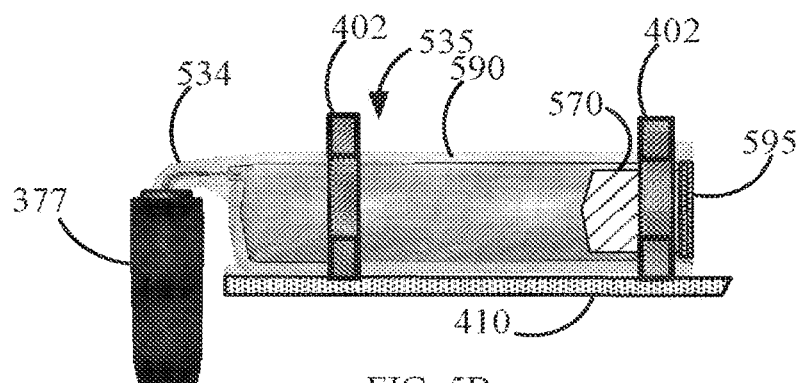

In the exemplary embodiment depicted in FIG. 5A an empty fluid reservoir 590 is coupled to a needle-bearing portion 534 to form a single integral self-injector cartridge unit 535. In some embodiments, cartridge unit 535 is sterile. In some embodiments, cartridge unit 535 is non-sterile. In some embodiments, cartridge unit 535 is sterilized, filled with an injectable in a sterile fashion and provided sterile, sealed and ready for use. As shown in the exemplary embodiments illustrated in FIG. 5B, a sterilely pre-filled cartridge unit 535 is coupled to support plate 410 by one or more fasteners 402 (FIG. 4A). In some embodiments, cartridge unit 535 comprises a plunger 570 and is sealed after filling for sterility with a seal 595. In some embodiments, cartridge unit 535 is delivered unsterile for sterilization and filling in an envelope e.g., a plastic blister 539. As shown in FIG. 5C, a fluid reservoir 550 e.g., 20 cc fluid reservoir, comprising a slip-on tip is mounted onto self-injector 500. In the exemplary embodiment shown in FIG. 5C tip 502 is shown to be inserted into a needle-bearing portion 506 in a fashion described elsewhere in the disclosure and will not be repeated. In the exemplary embodiment depicted in FIG. 5C, needle-bearing portion 506 comprises a coupling similar to that of fastener 504 and is reversibly coupled to support plate 410. In some embodiments, one or more fasteners 504 of a form and function of which is described elsewhere in the disclosure and will not be repeated are positioned along barrel 452 at least one of which abutting a finger flange 454 coupling a barrel 452 of fluid reservoir 450 to support plate 410. In some embodiments, when closed, fastener 504 provides sufficient friction against barrel 452 to prevent axial slippage and movement of barrel 452 in respect to support plate 410. Alternatively and optionally, in some embodiments, a fitting of a type described elsewhere in the disclosure may be fitted inside fastener 504 and provide sufficient friction against barrel 452 to prevent axial slippage and movement of barrel 452 in respect to support plate 410.

Alternatively and optionally and as shown in FIG. 5D, in some embodiments, a fastener 506 comprises a radial slot 508 along an internal wall 510 sized and fitted to accommodate a corresponding sized fluid reservoir finger flange 454. Alternatively and optionally and as shown in FIG. 5E, in some embodiments, a fastener of the type of fastener 504 comprises a fitting 512 fitted inside fastener 504 comprising a radial slot 514 along an internal wall of fitting 512 is sized and fitted to accommodate a corresponding sized fluid reservoir finger flange 454. In some embodiments, fitting 512 provides sufficient friction against finger flange 454 to prevent axial slippage and movement of barrel 452 in respect to support plate 410. In FIG. 5D a fluid reservoir plunger has been replaced with a plunger 570 configured to be driven by a self-injector 500 plunger driving system (not shown).

Alternatively and optionally, modular fluid reservoir-injector coupling system is shown in FIG. 5F coupling a small sized fluid reservoir 555 e.g., 5 cc fluid reservoir to self-injector 500. Fluid reservoir 555 slip-on tip is shown to be inserted into a needle-bearing portion 506 in a fashion described elsewhere in the disclosure and will not be repeated. In some embodiments, one or more fasteners 504 of a form and function of which is described elsewhere in the disclosure and will not be repeated are positioned along barrel 552 at least one of which abutting a finger flange 554 coupling a barrel 552 of fluid reservoir 555 to support plate 410. In some embodiments, when closed, fastener 504 provides sufficient friction against barrel 552 to prevent axial slippage and movement of barrel 552 in respect to support plate 410. Alternatively and optionally, in some embodiments, a fitting 430 of a type described elsewhere in the disclosure may be fitted inside fastener 504 and provide sufficient friction against barrel 552 to prevent axial slippage and movement of barrel 552 in respect to support plate 410.

Figure 6:
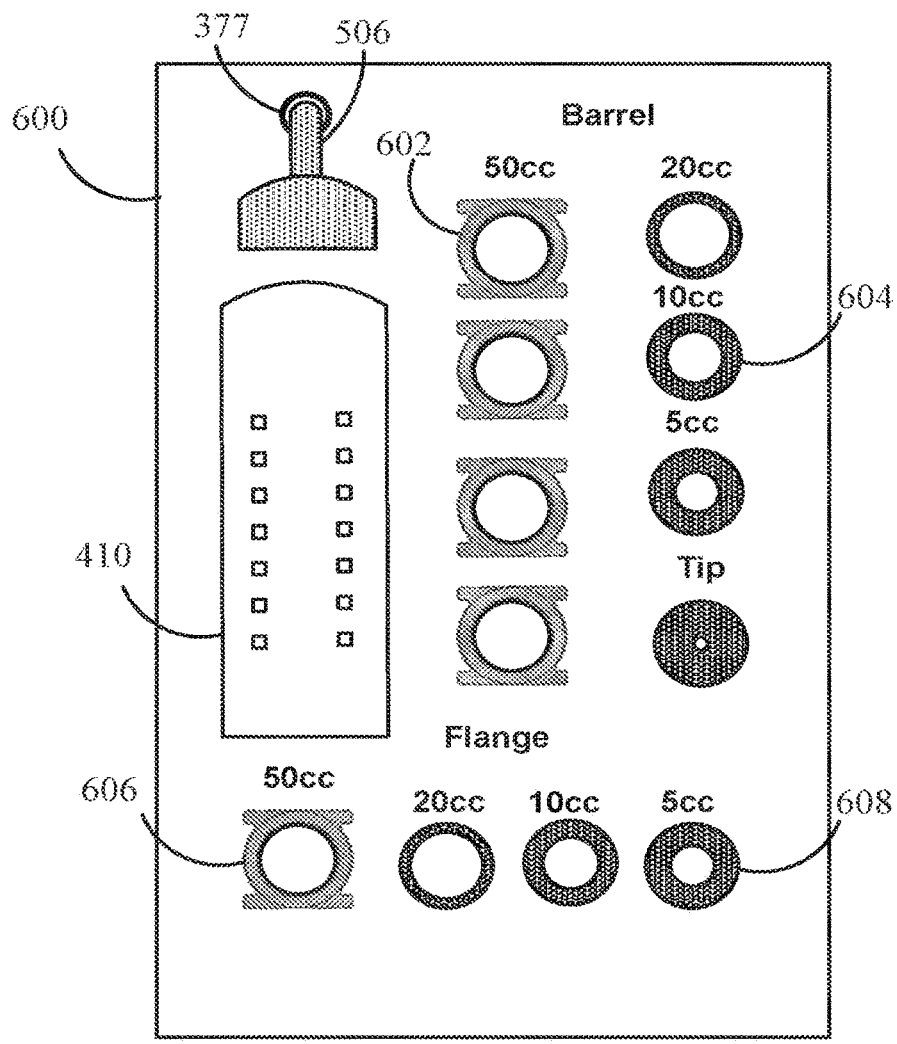
FIG. 6 is a plan view simplified illustration of a home kit for self-injection.

In the embodiment shown in FIG. 5F, a fitting 512 fitted inside fastener 504 is sized and fitted to accommodate corresponding sized fluid reservoir finger flange 554. As shown in FIG. 5G, needle-bearing portion 506 comprises a coupling 537 to support plate similar to that of fasteners 504 or any type of fastener coupling described elsewhere in the disclosure and is reversibly coupled to support plate 410. As shown in FIG. 5G, in some embodiments, a finger-flangeless fluid reservoir 590 is sealingly attached to needle-bearing portion 506. In the exemplary embodiment depicted in FIG. 5G, fluid reservoir 590 is a pre-filled vial attached to needle-bearing portion 506 and fitted with a fastener 402 (FIG. 4C) to be mounted onto support plate 410 as explained elsewhere in the disclosure. In some embodiments, needle-bearing portion 506 comprises a needle 202 protective cap 377. In some embodiments, fluid reservoir 590 is sealed for sterility with a seal 595. In some embodiments, pre-filled fluid reservoir 590 attached to needle-bearing portion 506 is delivered in an envelope e.g., a plastic blister 539. Reference is now made to FIG. 6, which is a plan view simplified illustration of a home kit for self-injection. As shown in FIG. 6, in some embodiments a kit 600 comprises a self-injector, represented in FIG. 6 by a modular support plate 410, a plurality of fasteners 602 and a variety of fittings 604 comprising various internal diameters.

Additionally and optionally, in some embodiments kit 600 may comprise markings that assist a user to select the correct fastener or fitting for the corresponding selected fluid reservoir. For example, in the exemplary embodiment depicted in FIG. 6, for a selected 50 cc fluid reservoir the user may select only fasteners to sufficiently couple the fluid reservoir to the self-injector. For a smaller sized fluid reservoir, e.g., 10 cc fluid reservoir the user may select a fastener and a fitting marked "10 cc" to be inserted into the fastener. In some embodiments, kit 600 comprises clearly marked indicators as to fitting sizes and types of fasteners and fittings e.g., "5 cc", "10 cc", "20 cc", "50 cc", "tip", "Flange", etc.

In some embodiments, a user would use kit 600 to couple a fluid reservoir to a self-injector by removing the self-injector from the kit and opening a cover to expose support plate 410. In some embodiments, the method further comprises coupling needle bearing portion 506 to the fluid reservoir. In some embodiments, needle bearing portion 506 comprises a needle protective cap 377. In some embodiments, the method further comprises selecting one or more fasteners 602 and sliding one or more fasteners on a barrel 452/552 of a fluid reservoir. Alternatively and optionally the method comprises coupling one or more fasteners 602 to support plate 410. Optionally, the method comprises inserting one or more fittings 604 into one or more fasteners 602 before sliding onto a barrel 452/552 of a fluid reservoir. Additionally and optionally, the method comprises selecting a finger flange fastener 606 and coupling the fluid reservoir flange to support plate 410. Optionally, the method comprises inserting one or more finger flange fittings 608 into one or more fasteners 602 before coupling the fluid reservoir flange to support plate 410. Optionally, the method comprises selecting at least one attachment points 412/416 and attaching a fastener 604/606 to the selected attachment points 412/416.

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A self-injector comprising:
   a plate;
   an adaptor comprising a rigid and bent fluid path, the adaptor configured to couple the rigid and bent fluid path to a tip of a fluid reservoir;
   a fastener configured to couple a body of the fluid reservoir to the plate, an inner diameter of the fastener being adjustable; and
   a retention lever configured to couple the fastener to the plate.

2. The self-injector of claim 1, wherein a distance between the adaptor and the fastener is adjustable.

3. The self-injector of claim 1, wherein the retention lever is configured to releasably couple the fastener to the plate.

4. The self-injector of claim 1, wherein the fastener comprises a recess configured to receive the retention lever.

5. The self-injector of claim 1, wherein the fastener comprises a plurality of recesses configured to receive the retention lever for adjustment of the fastener.

6. The self-injector of claim 1, where the fastener comprises a pair of legs configured to receive the body of the fluid reservoir therebetween.

7. The self-injector of claim 1, further comprising a hinge configured to pivotably couple the fastener to the plate.

8. A self-injector comprising:
a support plate having a plurality of attachment points;
an adaptor comprising a rigid and bent fluid path, the adaptor configured to couple the rigid and bent fluid path to at least a tip of a fluid reservoir;
a fastener configured to couple to a body of the fluid reservoir and to at least one of the attachment points; and
a retention cantilever configured to releasably couple the fastener to the support plate.

9. The self-injector of system claim 8, wherein the adaptor is configured to couple to at least one of the attachment points.

10. The self-injector of system claim 8, wherein the attachment points are distributed on the support plate at varying distances from the adaptor.

11. The self-injector system claim 10, wherein the varying distances correspond to varying lengths of the fluid reservoir.

12. The self-injector of system claim 8, wherein an internal diameter of the fastener is adjustable.

13. The self-injector of system claim 8, further comprising a fitting configured to fit along an inner surface of the fastener.

14. The self-injector of system claim 13, wherein the fitting reduces an inner diameter of the fastener.

15. An add-on for a self-injector, the add-on comprising:
an adaptor comprising a rigid and bent fluid path, the adaptor being configured to couple the rigid and bent fluid path to a tip of a fluid reservoir; and
a fastener configured to couple a body of the fluid reservoir to a body of the self-injector, an inner diameter of the fastener being adjustable,
wherein a distance between the adaptor and the fastener is adjustable.

16. The add-on of claim 15, further comprising a fitting configured to fit along an inner surface of the fastener.

17. The add-on of claim 16, wherein the fitting reduces an inner diameter of the fastener.

18. The add-on of claim 15, wherein at least a portion of the fastener is made of a plastic material.

19. The add-on of claim 15, wherein at least a portion of the fluid reservoir is made of a glass or a plastic material.

20. The add-on of claim 15, wherein the rigid and bent fluid path comprises a hollow needle.

21. The add-on of claim 15, wherein the rigid and bent fluid path is bent at a 90-degree angle.

22. The add-on of claim 15, wherein the fluid reservoir is a prefilled cartridge or a vial.

23. The add-on of claim 15, wherein the add-on is sterilizable en bloc.

24. The add-on of claim 15, wherein the adaptor further comprises an adaptor coupling configured to couple the add-on to the self-injector.

25. The add-on of claim 24, wherein the adaptor coupling is a Luer lock coupling or a vial adapter.

26. The add-on of claim 24, wherein the adaptor coupling is a slide-on fluid reservoir coupling.

27. An add-on for a self-injector, the add-on comprising:
an adaptor comprising a rigid and bent fluid path, the adaptor being configured to couple the rigid and bent fluid path to a tip of a fluid reservoir;
a fastener configured to couple a body of the fluid reservoir to a body of the self-injector; and
a fitting configured to fit along an inner surface of the fastener,
wherein an inner diameter of the fastener is adjustable.

28. The add-on of claim 27, wherein the fitting reduces the inner diameter of the fastener.

\* \* \* \* \*